US009187457B2

(12) United States Patent
Gershengorn et al.

(10) Patent No.: US 9,187,457 B2
(45) Date of Patent: *Nov. 17, 2015

(54) LOW MOLECULAR WEIGHT THYROID STIMULATING HORMONE RECEPTOR (TSHR) AGONISTS

(71) Applicants: The United States of America as represented by the Secretary of the Department of Health and Human Services, Washington, DC (US); Forschungsverbund Berlin E.V., Berlin-Adlershof (DE)

(72) Inventors: Marvin C. Gershengorn, Washington, DC (US); Susanne Neumann, Bethesda, MD (US); Bruce M. Raaka, Rockville, MD (US); Craig J. Thomas, Gaithersburg, MD (US); James Inglese, Bethesda, MD (US); Noel T. Southall, Chevy Chase, MD (US); Steven Titus, Elkridge, MD (US); Wei Zheng, Potomac, MD (US); Wenwei Huang, Rockville, MD (US); Gerd Krause, Berlin (DE); Gunnar Kleinau, Berlin (DE)

(73) Assignees: The United States of America as represented by the Secretary of the Department of Health and Human Services, Washington, DC (US); Forschungsverbund Berlin E.V., Berlin-Adlershof (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,330

(22) Filed: May 17, 2013

(65) Prior Publication Data

US 2013/0251631 A1    Sep. 26, 2013

Related U.S. Application Data

(63) Continuation of application No. 13/125,045, filed as application No. PCT/US2008/011958 on Oct. 20, 2008, now Pat. No. 8,741,259.

(51) Int. Cl.
*A61K 51/00* (2006.01)
*C07D 239/88* (2006.01)
(Continued)

(52) U.S. Cl.
CPC ............ *C07D 405/06* (2013.01); *A61K 31/517* (2013.01); *A61K 49/0004* (2013.01);
(Continued)

(58) Field of Classification Search
CPC .................................................. A61K 31/517
See application file for complete search history.

(56) References Cited

U.S. PATENT DOCUMENTS 6,924,295 B2    8/2005    Tajima et al.
7,220,864 B2    5/2007    Tajima et al.
(Continued)

FOREIGN PATENT DOCUMENTS

CA    2568622    12/2005
EP    1 354 879    12/2001
(Continued)

OTHER PUBLICATIONS

Abe et al., "TSH is a Negative Regulator of Skeletal Remodeling," *Cell* 115:151-162, Oct. 17, 2003.
(Continued)

*Primary Examiner* — Scott Long
*Assistant Examiner* — Sarah Alawadi
(74) *Attorney, Agent, or Firm* — Klarquist Sparkman, LLP

(57) ABSTRACT

Disclosed are oxo-hydroquinazolines that are useful as selective TSHR agonists. The compounds may be used for detecting or treating thyroid cancer, or treating a bone degenerative disorder.

21 Claims, 4 Drawing Sheets

(51) Int. Cl.

| | | |
|---|---|---|
| *C07D 217/24* | (2006.01) | |
| *A61K 31/47* | (2006.01) | |
| *A61P 35/00* | (2006.01) | |
| *A61K 31/167* | (2006.01) | |
| *A61K 31/517* | (2006.01) | |
| *C07C 233/01* | (2006.01) | |
| *C07D 405/06* | (2006.01) | |
| *C07D 239/91* | (2006.01) | |
| *C07D 401/06* | (2006.01) | |
| *C07D 405/14* | (2006.01) | |
| *C07D 487/04* | (2006.01) | |
| *A61K 49/00* | (2006.01) | |

(52) U.S. Cl.
CPC ............. *A61K51/00* (2013.01); *C07D 239/91* (2013.01); *C07D 401/06* (2013.01); *C07D 405/14* (2013.01); *C07D 487/04* (2013.01)

(56) References Cited

U.S. PATENT DOCUMENTS

| | | |
|---|---|---|
| 7,223,767 B2 | 5/2007 | Clark et al. |
| 7,229,990 B2 | 6/2007 | Timmers et al. |
| 7,317,006 B2 | 1/2008 | Hanssen et al. |
| 7,375,109 B2 | 5/2008 | Hanssen et al. |
| 2005/0038052 A1 | 2/2005 | Clark et al. |
| 2005/0250824 A1 | 11/2005 | Tajima et al. |
| 2006/0025400 A1 | 2/2006 | Askew, Jr. et al. |
| 2006/0030573 A1 | 2/2006 | Boyce et al. |
| 2006/0052303 A1 | 3/2006 | Sampath et al. |
| 2006/0069106 A1 | 3/2006 | Fu et al. |
| 2006/0229324 A1 | 10/2006 | Itai et al. |
| 2008/0167329 A1 | 7/2008 | Barrow et al. |
| 2008/0293699 A1 | 11/2008 | Reed et al. |

FOREIGN PATENT DOCUMENTS

| | | |
|---|---|---|
| WO | WO 2007/075906 | 12/2006 |
| WO | WO 2007/136776 | 11/2007 |
| WO | WO 2008/086730 | 1/2008 |
| WO | WO 2008/153760 | 12/2008 |

OTHER PUBLICATIONS

Jäschke et al., "A Low Molecular Weight Agonist Signals by Binding to Transmembrane Domain of Thyroid-stimulating Hormone Receptor (TSHR) and Luteinizing Hormone/Chorionic Gonadotropin Receptor (LHCGR)," *Journal of Biological Chemistry* 281(15):9841-9844, Apr. 14, 2006.

Martini et al., "The Effects of Recombinant TSH on Bone Turnover Markers and Serum Osteoprotegerin and RANKL Levels," *Thyroid* 18(4):455-460, 2008.

Moore et al., "Evaluation of Small-Molecular Modulators of the Luteinizing Hormone/Choriogonadotropin and Thyroid Stimulating Hormone Receptors: Structure —Activity Relationships and Selective Binding Patterns," *Journal of Medicinal Chemistry* 49:3888-3896, 2006 (Published online May 24, 2006).

Neumann et al., "A Low-Molecular-Weight Antagonist for the Human Thyrotropin Receptor with Therapeutic Potential for Hyperthyroidism," *Endocrinology* 149(12):5945-5950, 2008 (Published Online Jul. 31, 2008).

Neumann et al., "Small-molecule agonists for the thyrotropin receptor stimulate thyroid function in human thyrocytes and mice," *PNAS* 106(30):12471-12476, Jul. 28, 2009.

Sun et al., "Intermittent recombinant TSH injections prevent ovariectomy-induced bone loss," *PNAS* 105(11):4289-4294, Mar. 18, 2008.

Titus et al., "Quantitative High-Throughput Screening Using a Live-Cell cAMP Assay Identifies Small-Molecule Agonists of the TSH Receptor," *Journal of Biomolecular Screening* 13(2):120-127, Feb. 2008 (Published online Jan. 23, 2008).

International Search Report from PCT Application No. PCT/US2008/011958 dated Jul. 16, 2009.

Written Opinion of the International Searching Authority from PCT Application No. PCT/US2008/011958 dated Jul. 16, 2009.

PubChem Compound Summary—CID 17757102; Create Date Nov. 30, 2007.

PubChem Compound Summary—CID 661788; Create Date Jun. 29, 2005.

PubChem Compound Summary—CID 17757314; Create Date Nov. 30, 2007.

PubChem Compound Summary—CID 2887926; Create Date Jul. 29, 2005.

PubChem Compound Summary—CID 16759579; Create Date Nov. 9, 2007.

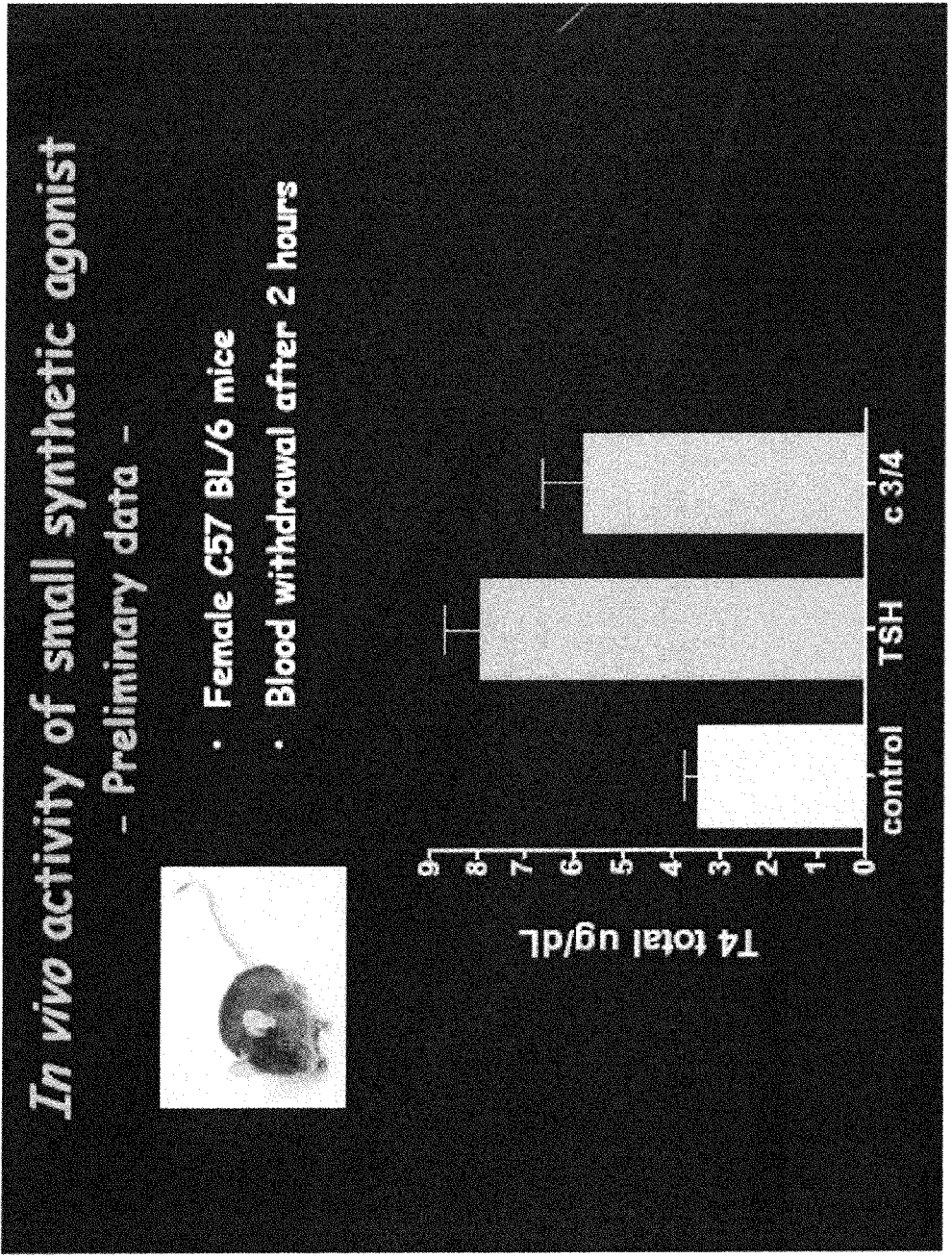

LOW MOLECULAR WEIGHT THYROID STIMULATING HORMONE RECEPTOR (TSHR) AGONISTS

CROSS REFERENCE TO RELATED APPLICATIONS

This is a continuation of U.S. application Ser. No. 13/125,045, filed Apr. 19, 2011, which is the U.S. National Stage of International Application No. PCT/US2008/011958, filed Oct. 20, 2008, published in English under PCT Article 21(2), both of which are herein incorporated by reference in their entirety.

FIELD

Disclosed herein are compounds that are thyroid stimulating hormone receptor (TSHR) agonists for diagnostic, analytical and therapeutic purposes.

BACKGROUND

Thyroid-stimulating hormone (TSH) is a heterodimeric glycoprotein hormone that regulates thyroid homeostasis. TSH is involved in the growth and function of thyroid follicular cells. Cellular responses to TSH are mediated via the TSH receptor (TSHR) which is a distinct seven transmembrane-spanning receptor. TSHR is the major regulator of thyroid gland (and most thyroid cancer) function and is expressed in bone and adipocytes (fat) precursor cells. Activation of TSHR by its endogenous hormone TSH is required for normal thyroid homeostasis but may also regulate bone and fat biology.

The thyroid gland is, as is well known, one site of metabolic control within the body. Cancer of the thyroid gland is not particularly common, but the high rate of disease re-occurrence necessitates long term surveillance. Usually, during treatment for cancer of the thyroid, the majority of the thyroid tumor is removed, but a small amount often remains that must be treated by radioactive iodide therapy. Indeed, thyroid cancer is characterized by a high likelihood of relapses in up to 30% of patient, even after successful therapy. Therefore, follow-up screening is necessary.

Following surgery, it is necessary to treat the patient with thyroid hormone, as the patient will no longer produce this. One role of the thyroid gland is to take up iodine from the body. Hence, it should be possible to treat any remaining tumor cells with radioactive iodide. Unfortunately, though, thyroid cancer cells do not take up iodine well. So, in order for the radioactive iodine to work, the patient has to either be treated with recombinant TSH or have thyroid hormone treatment withdrawn in order to elevate natural TSH levels, to stimulate iodide uptake. Withdrawal of thyroid hormone has quite unpleasant side effects for the patient, particularly fatigue, muscle cramps, puffiness and constipation. Thus, at the present time, recombinant human TSH (rhTSH, Thyrogen®, Genzyme) is used clinically for screening after surgery in patients with well-differentiated thyroid cancer. However, rhTSH is a dimeric glycoprotein molecule that is made by genetic engineering in human cells. It is difficult to produce, requires stringent quality control and must be administered parenterally.

SUMMARY

Disclosed herein are compounds having formula I:

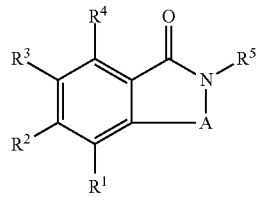

or a pharmaceutically acceptable salt thereof, wherein:
$R^1$-$R^4$ are each independently H, hydroxyl, alkyl, alkoxy, aminocarbonyl, or halogen;
$R^5$ is H, alkyl, aryl, aralkyl, or aminocarbonyl;
A represents —N=C($R^{15}$)— (wherein a bond at the left end bonds to the benzene ring of formula I above and a bond at the right end bonds to the nitrogen heteroatom of formula I above) or —NH—CH($R^{15}$)— (wherein a bond at the left end bonds to the benzene ring of formula I above and a bond at the right end bonds to the nitrogen heteroatom of formula I above);
$R^{15}$ is represented by formula II:

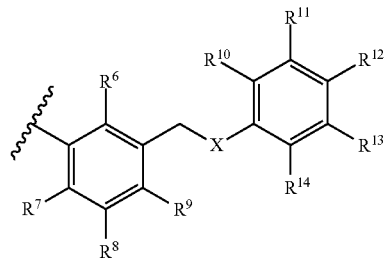

wherein:
$R^6$-$R^9$ are each independently H, hydroxyl, alkyl, or alkoxy;
$R^{10}$-$R^{14}$ are each independently H, hydroxyl, alkyl, alkoxy, or aminocarbonyl; and
X is O, S or N(H);
with the proviso that the compound of formula I is not (Compound 1)

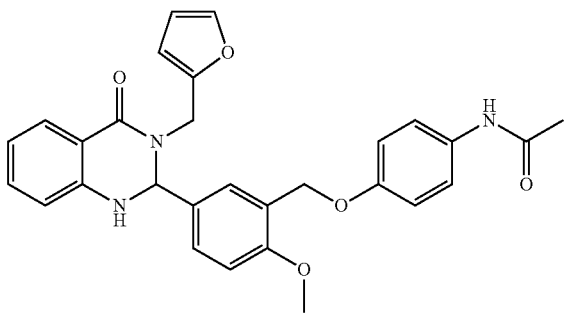

Also disclosed are additional Compounds of formula VI:

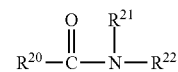

wherein $R^{20}$ is aryl or heteroaryl; $R^{21}$ is aryl or heteroaryl; $R^{22}$ is $R^{15}$ of formula II as shown in claim in claim 1, heteroaryl, or aryl.

Also disclosed herein is a method for detecting thyroid cancer in a subject, comprising administering to the subject a diagnostically effective amount of at least one compound of formula I:

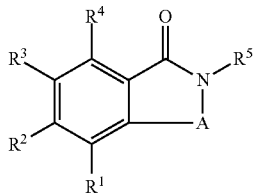

or a pharmaceutically acceptable salt thereof, wherein:
$R^1$-$R^4$ are each independently H, hydroxyl, alkyl, alkoxy, aminocarbonyl, or halogen;
$R^5$ is H, alkyl, aryl, aralkyl, or aminocarbonyl;
A represents —N=C($R^{15}$)— (wherein a bond at the left end bonds to the benzene ring of formula I above and a bond at the right end bonds to the nitrogen heteroatom of formula I above) or —NH—CH($R^{15}$)— (wherein a bond at the left end bonds to the benzene ring of formula I above and a bond at the right end bonds to the nitrogen heteroatom of formula I above);
$R^{15}$ is represented by formula II:

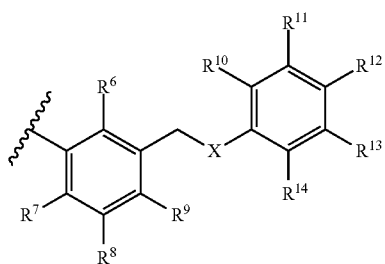

wherein:
$R^6$-$R^9$ are each independently H, hydroxyl, alkyl, or alkoxy;
$R^{10}$-$R^{14}$ are each independently H, hydroxyl, alkyl, alkoxy, or aminocarbonyl; and
X is O, S or N(H);
or at least one compound of formula VI.

A further embodiment disclosed herein involves a method for treating or preventing a bone degenerative disorder comprising administering a therapeutically effective amount of at least one compound of formula I or at least one compound of formula VI.

Also disclosed herein is a method for treating thyroid cancer in a subject, comprising administering to the subject a therapeutically effective amount of at least one compound of formula I or at least one compound of formula VI.

An additional embodiment disclosed herein involves a method for activating a thyroid stimulating hormone receptor in an assay, comprising contacting the thyroid stimulating hormone receptor with at least one compound of formula I or at least one compound of formula VI.

Also disclosed herein are pharmaceutical compositions comprising a pharmaceutically acceptable carrier and at least one compound of formula I or at least one compound of formula VI.

The foregoing and other objects, features, and advantages will become more apparent from the following detailed description, which proceeds with reference to the accompanying figures.

BRIEF DESCRIPTION OF THE DRAWINGS

FIG. 4 is a graph of data of in vivo activity of a compound disclosed herein in a mouse model.

DETAILED DESCRIPTION

Figure 1:
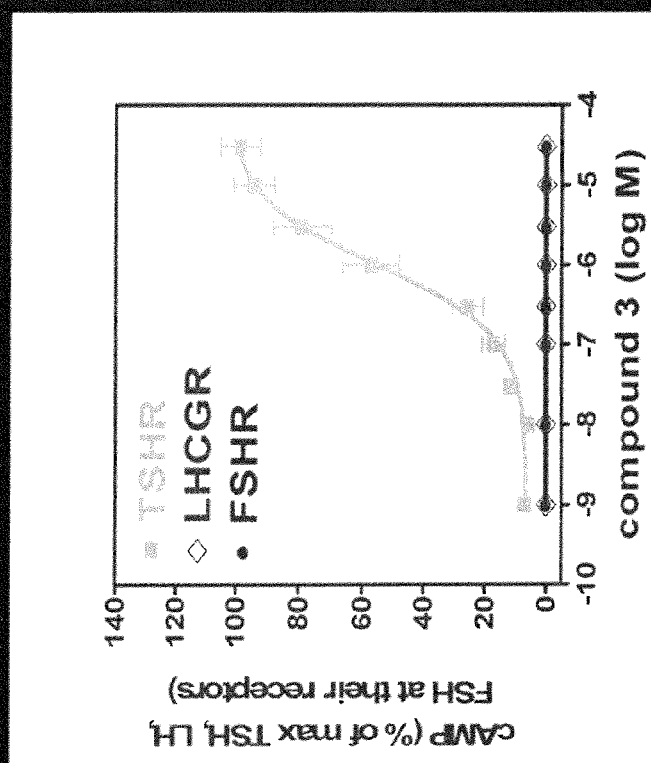
FIG. 1 is graph depicting data showing that a compound disclosed herein is a full and selective agonist.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R^1$, $R^2$, $R^3$, $R^4$, $R^5$, $R^6$, $R^7$, $R^8$, $R^9$, n, X and Y, used throughout the disclosure are the same variables as previously defined unless stated to the contrary.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Optional" or "optionally" means that the subsequently described event or circumstance can but does not need to occur, and that the description includes instances where said event or circumstance occurs and instances where it does not.

"Derivative" refers to a compound or portion of a compound that is derived from or is theoretically derivable from a parent compound.

The term "subject" includes both human and veterinary subjects.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease or condition, for example, in a subject who is at risk for a disease such as a hormone receptor mediated disorder, particularly a thyroid disorder, such as a hyperthyroid or hypothyroid disorder. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Saturated or unsaturated" includes substituents saturated with hydrogens, substituents completely unsaturated with hydrogens and substituents partially saturated with hydrogens.

The term "acyl" refers group of the formula RC(O)— wherein R is an organic group.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkenyl" refers to a hydrocarbon group of 2 to 24 carbon atoms and structural formula containing at least one carbon-carbon double bond.

The term "alkynyl" refers to a hydrocarbon group of 2 to 24 carbon atoms and a structural formula containing at least one carbon-carbon triple bond.

The terms "halogenated alkyl" or "haloalkyl group" refer to an alkyl group as defined above with one or more hydrogen atoms present on these groups substituted with a halogen (F, Cl, Br, I).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl amino" refers to alkyl groups as defined above where at least one hydrogen atom is replaced with an amino group.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

Pharmaceutically acceptable prodrugs refer to compounds that are metabolized, for example, hydrolyzed or oxidized, in the subject to form an antiviral compound of the present disclosure. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. In general the prodrug compounds disclosed herein possess hormone receptor modulating activity and/or are metabolized or otherwise processed in vivo to form a compound that exhibits such activity.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999.

When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

I. Compounds

Disclosed herein are low molecular weight (for example, less than 1000 daltons) compounds that activate TSHR. These compounds may be orally administered. Data is presented below demonstrating the efficacy of the compounds in cells expressing human TSHRs in culture. Certain compounds disclosed herein are selective agonists for TSHR (i.e, the compounds do not activate or modulate other hormone receptors, particularly LHCGR and FSHR). The compounds also may be full agonists for TSHR.

The TSHR agonists disclosed herein enhance or activate a TSH signaling pathway. The TSHR agonists may stimulate the TSHR-mediated signaling by themselves, or stimulate TSHR-mediated signaling by enhancing the biological activity of endogenous TSH or another administered (i.e., exogenous) TSHR agonist. Although not bound by any theory, it is believed that in certain embodiments the TSHR agonists disclosed herein specifically bind TSHR (in particular, the transmembrane domain of TSHR) which then transduces TSHR-mediated intracellular signaling in thyrotrophs or other cells naturally expressing TSHR or cells modified to express TSHR. The term "specific binding" and its cognates refer to an interaction with an affinity constant $K_A$ of less than 100 micromolar, particular 100 nanomolar, and preferably less than 50 nanomolar.

Examples of the compounds are represented by formula I:

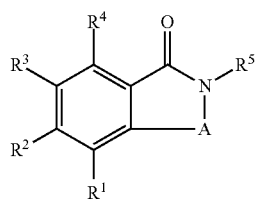

or a pharmaceutically acceptable salt thereof, wherein:

$R^1$-$R^4$ are each independently H, hydroxyl, alkyl, alkoxy, aminocarbonyl, or halogen;

$R^5$ is H, alkyl, aryl, aralkyl, or aminocarbonyl;

A represents —N═C($R^{15}$)— (wherein a bond at the left end bonds to the benzene ring of formula I above and a bond at the right end bonds to the nitrogen heteroatom of formula I above) or —NH—CH($R^{15}$)— (wherein a bond at the left end bonds to the benzene ring of formula I above and a bond at the right end bonds to the nitrogen heteroatom of formula I above);

$R^{15}$ is represented by formula II:

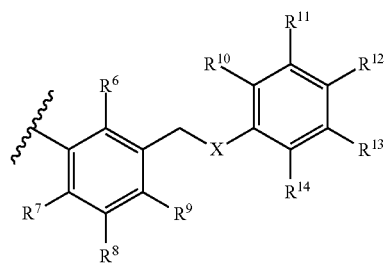

wherein:

$R^6$-$R^9$ are each independently H, hydroxyl, alkyl, or alkoxy;

$R^{10}$—$R^{14}$ are each independently H, hydroxyl, alkyl, alkoxy, or aminocarbonyl; and X is O, S, or N(H).

In certain embodiments, a compound having a structure of (Compound 3)

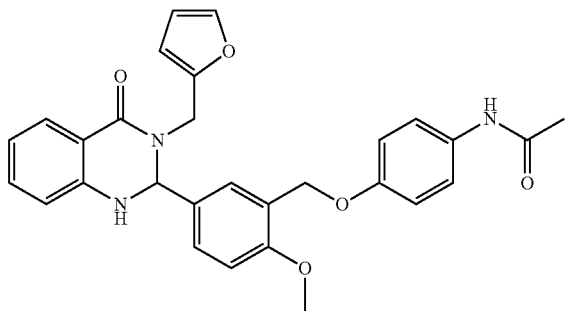

is not included in formula I.

In certain embodiments, $R^1$-$R^4$ are each independently H, hydroxyl or acetamido. According to preferred examples, each of $R^1$-$R^4$ is H; one of $R^1$-$R^4$ is acetamido (preferably $R^3$) and the remaining $R^1$-$R^4$ are each H; or one of $R^1$-$R^4$ is hydroxyl (preferably $R^4$) and the remaining $R^1$-$R^4$ are each H.

In certain embodiments, $R^5$ is an aralkyl such as —$C_1$-$C_4$ alkyl —Ar (wherein Ar is a 6-member or 5-member ring). According to preferred examples, $R^5$ is —$CH_2$-Ph (wherein Ph is a phenyl or substituted phenyl group); or —$CH_2$-heteroAr (wherein heteroAr is an aryl ring that includes at least one heteroatom such as O, N or S (e.g., a furyl group).

In certain embodiments, A represents —N═C($R^{15}$)— (wherein a bond at the left end bonds to the benzene ring of formula I above and a bond at the right end bonds to the nitrogen heteroatom of formula I above) resulting in a structure of formula IV:

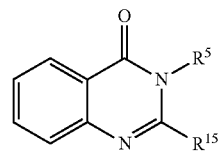

(although not shown in formula V, $R^1$-$R^4$ are also present as shown in formula I).

In other embodiments, A represents —NH—CH($R^{15}$)— (wherein a bond at the left end bonds to the benzene ring of formula I above and a bond at the right end bonds to the nitrogen heteroatom of formula I above) resulting in a structure of formula V;

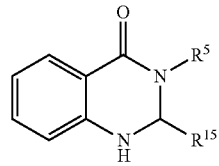

(although not shown in formula V, $R^1$-$R^4$ are also present as shown in formula I).

In certain embodiments, $R^6$-$R^8$ are each H and $R^9$ is alkoxy (particularly methoxy).

In certain embodiments, $R^{10}$, $R^{11}$, $R^{13}$, and $R^{14}$ are each H and $R^{12}$ is acetamido.

Preferably, $R^{15}$ is represented by formula III:

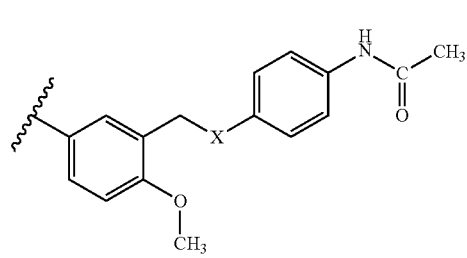

wherein X is O or S, preferably O.

Illustrative compounds include:

(Compound 3/2)

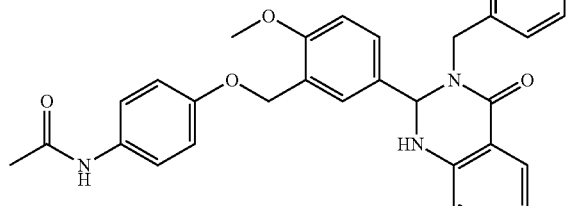

(Compound 3/5)

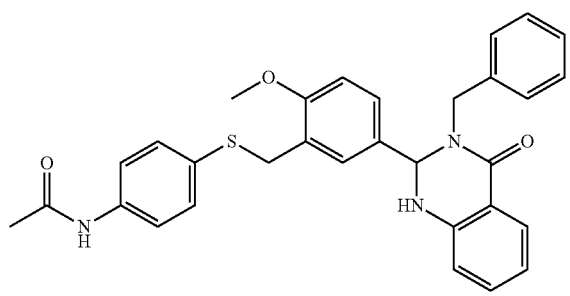

(Compound 3/1)

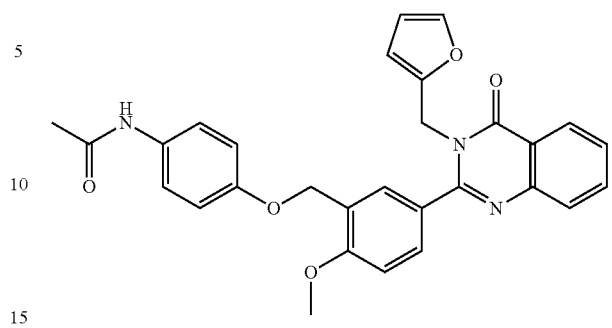

(Compound 3/4)

(Compound 3/3)

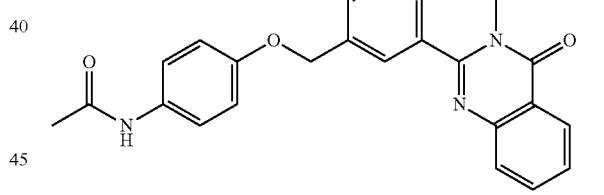

According to another embodiment, examples of the additional TSHR agonists are represented by formula VI:

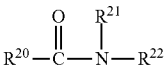

wherein $R^{20}$ is aryl or heteroaryl; $R^{21}$ is aryl or heteroaryl; $R^{22}$ is $R^{15}$ of formula II, heteroaryl, or aryl. According to a preferred embodiment, $R^{21}$ is benzyl and $R^{22}$ is $R^{15}$ of formula II (particularly formula III).

II. General Synthesis

The compounds disclosed herein may be generally synthesized as described below. With reference to Scheme 1,2-aminobenzamides (1) were prepared by either amide couplings (step i) of 2-aminobenzoic acids with different amines or reactions of isatoic anhydrides with amines (step ii).

Scheme 1

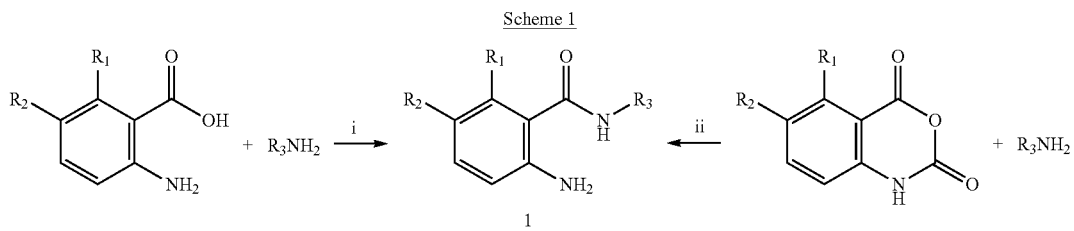

Reagents and conditions: (i) DMC, DIPEA, r.t. 12 h; (ii) ACN, r.t.-50° C.

With reference to Scheme 2, reactions of benzyl chlorides 2 with different phenols or thiophenols under microwave irradiation (step i) generated aldehydes 3. Condensations of aldehydes 3 with 2-aminobenzamides 1 yielded 2,3-dihydroquinazolin-4-ones 4. The 2,3-dihydroquinazolin-4-ones 4 were rapidly oxidized by DDQ at room temperature to produce quinazolin-4-ones 5.

Scheme 2

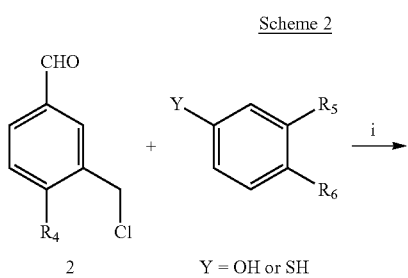

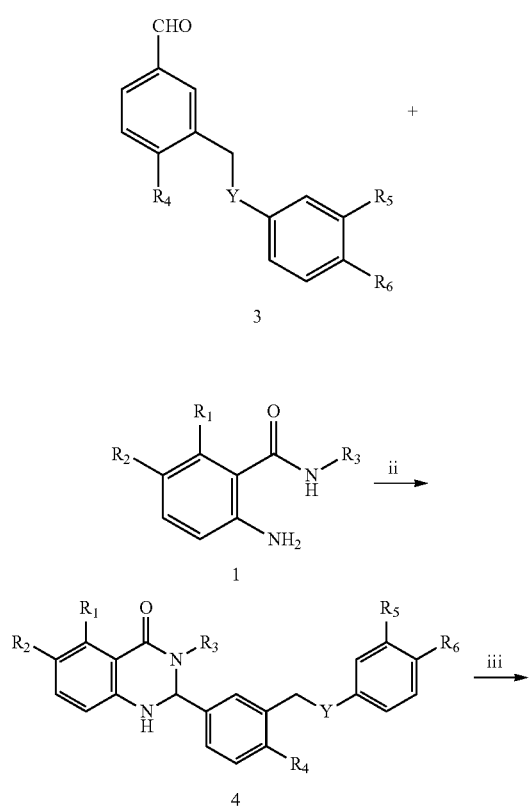

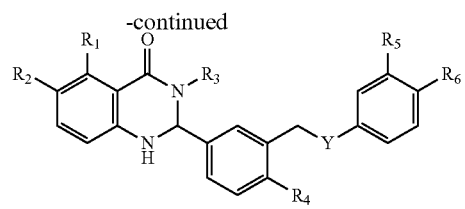

Reagents and conditions: (i) K$_2$CO$_3$, DMA, microwave heating, 150° C., 10 min; (ii) Yb(OTf)$_3$, DMA, microwave heating, 200° C., 10 min; (iii) DDQ, r.t. 1 h III. Compositions, Administration and Use of the Disclosed Compounds The compounds disclosed herein may be useful for thyroid cancer screening, treating thyroid cancer, treating nodular goiter, TSH stimulation to enhance PET scanning and chemotherapy treatment, differential diagnosis of congenital hypothyroidism, treating osteoporosis (e.g., inhibiting bone loss) and treating overweight or obesity (e.g, increase metabolic rate of fat tissue). Illustrative uses of the compounds disclosed herein include:

agonist thyroglobulin (Tg) testing may be used in patients with an undetectable Tg on thyroid suppression therapy to exclude the diagnosis of residual or recurrent thyroid cancer;

agonist treatment may be used in combination with radio-iodine (131I) to ablate thyroid remnants following near-total thyroidectomym in patients without evidence of metastatic disease;

agonist testing may be used in patients requiring serum Tg testing and radioiodine imaging who are unwilling to undergo thyroid hormone withdrawal testing and whose treating physician believes that use of a less sensitive test is justified; or agonist treatment and testing may be used in patients who are either unable to mount an adequate endogenous TSH response to thyroid hormone withdrawal or in whom withdrawal is medially contraindicated.

According to one embodiment the compounds disclosed herein (including Compound I) are useful for thyroid cancer screening. Radioiodine is used for detection of thyroid cancer cells and to increase test sensitivity the uptake of radioiodine must be enhanced. Administration of a TSHR agonist disclosed herein can increase the iodine uptake of thyroid cells. For example, the TSHR agonists disclosed herein could replace recombinant human TSH (rhTSH, Thyrogen®, Genzyme) for clinically screening for residual or recurring thyroid cancer after surgery (e.g., thyroidectomy) in patients with well-differentiated thyroid cancer. The TSHR agonists disclosed herein also can be used as an adjunct diagnostic for serum thyroglobulin (TG) testing.

Also disclosed are methods for treating or preventing bone degenerative disorders that include administering a therapeutically effective amount of at least one TSHR agonist compound disclosed herein. The disorders treated or prevented include, for example, osteopenia, osteomalacia, osteoporosis, osteomyeloma, osteodystrophy, Paget's disease, osteogenesis imperfecta, bone sclerosis, aplastic bone disorder, humoral hypercalcemic myeloma, multiple myeloma and bone thinning following metastasis. The disorders treated or prevented further include bone degenerative disorders associated with hypercalcemia, chronic renal disease (including end-stage renal disease), kidney dialysis, primary or secondary hyperparathyroidism, and long-term use of corticosteroids.

The compounds disclosed herein may be included in pharmaceutical compositions (pharmaceutical compositions include therapeutic, diagnostic and prophylactic formulations), typically combined together with one or more pharmaceutically acceptable vehicles or carriers and, optionally, other therapeutic or diagnostic ingredients (for example, a radioiodine). Such pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomoles (under standard conditions) would be administered at about twice the dosage of particles with a release rate of 10 nanomoles.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject. The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Examples

General Materials and Methods:

All commercially available reagents and solvents were purchased and used without further purification. All microwave reactions were carried out in a sealed microwave vial equipped with a magnetic stir bar and heated in a Biotage Initiator Microwave Synthesizer. All compounds for biological testing were purified using a Waters semi-preparative HPLC equipped with a Phenomenex Luna® C18 reverse phase (5 micron, 30×75 mm) column having a flow rate of 45 mL/min. The mobile phase was a mixture of acetonitrile and H$_2$O each containing 0.1% trifluoroacetic acid. During purification, a gradient of 30% to 80% acetonitrile over 8 minutes was used with fraction collection triggered by UV detection (220 nM). Pure fractions passed through PL-HCO$_3$ MP SPE (Varian) to remove trifluoroacetic acid and concentrated under vacuum on a lyophilizer. $^1$H spectra were recorded using an Inova 400 (100) MHz spectrometer (Varian). Chemical shifts are reported in δ (ppm) units using $^1$H (residual) from CDCl$_3$ (7.27) as internal standard. Data are reported as follows: chemical shift, multiplicity (s=singlet, d=doublet, t=triplet, q=quartet, m=multiplet, br=broad), coupling constant, and integration. Samples were analyzed for purity on an Agilent 1200 series LC/MS equipped with a Zorbax™ Eclipse XDB-C18 reverse phase (5 micron, 4.6×150 mm) column having a flow rate of 1.1 mL/min. The mobile phase was a mixture of acetonitrile and H$_2$O each containing 0.05% trifluoroacetic acid. A gradient of 5% to 100% acetonitrile over 8 minutes was used during analytical analysis. High-resolution mass spectroscopy measurements were performed on a Agilent 6210 Electrospray TOF mass spectrometer.

General Synthetic Procedures

The following general procedures were used to synthesize compounds having different but analogous structures. One of skill in the art will recognize how to modify these general procedures if necessary to accomplish the desired transformations.

General Procedure for the Synthesis of 2-Aminobenzamides from Isatoic Anhydride:

To a solution of isatoic anhydride (0.163 g, 1.0 mmol, 1.0 equiv) in 10 mL of anhydrous acetonitrile was added amines (1.05 mmol, 1.05 equiv) at room temperature. The resulting mixture was stirred at room temperature for 2 hours and heated at 50° C. for 4 hours. Then, it was concentrated in vacuo yielded the products as solids in 90-99% yields 2-Amino-N-benzylbenzamide

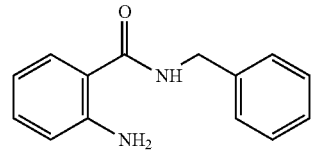 [SMILES: Nc1ccccc1C(=O)NCc1ccccc1]

$^1$H NMR (400 MHz, CHLOROFORM-d) δ 4.61 (s, 1H), 4.63 (s, 1H), 5.58 (br. s., 2H), 6.33 (br. s., 1H), 6.62-6.66 (m, 1H), 6.69-6.71 (m, 1H), 7.19-7.25 (m, 1H), 7.28-7.43 (m, 6H); LCMS: (electrospray+ve), m/z 227.1 (MH)$^+$; HPLC: $t_R$=4.38 min, UV$_{254}$=96%.

2-Amino-N-(furan-2-ylmethyl)benzamide

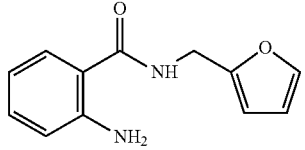 [SMILES: Nc1ccccc1C(=O)NCc1ccco1]

$^1$H NMR (400 MHz, CHLOROFORM-d) δ 4.60 (s, 1H), 4.61 (s, 1H), 5.57 (br. s., 2H), 6.24-6.42 (m, 3H), 6.59-6.74 (m, 2H), 7.16-7.25 (m, 1H), 7.33-7.39 (m, 2H); LCMS: (electrospray+ve), m/z 217.1 (MH)$^+$; HPLC: $t_R$=3.77 min, UV$_{254}$=98%.

2-Amino-N-benzyl-6-methoxybenzamide

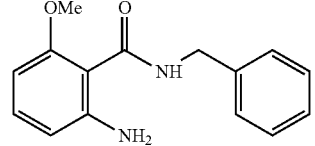 [SMILES: COc1cccc(N)c1C(=O)NCc1ccccc1]

To a solution of 2-amino-6-methoxybenzoic acid (0.841 g, 5.0 mmol, 1.0 equiv), benzylamine (0.643 g, 6.0 mmol, 1.2 equiv), and diisopropylethylamine (1.935 g, 15.0 mmol, 3.0 equiv) in 50 mL of dichloromethane was added 2-chloro-1,3-dimethylimidazolinium chloride (1.099 g, 6.5 mmol, 1.3 equiv) at room temperature. The mixture was stirred at room temperature for 6 hours, poured into water, and extracted with dichloromethane. The organic solution was successively washed with aqueous saturated NaHCO$_3$ and water. The organic layer was dried over MgSO$_4$ and the solvent was removed by rotary evaporator. The residue was purified by column chromatography (silica gel, 2% 2.0 M ammonia MeOH solution in CH$_2$Cl$_2$) to give 2-Amino-N-benzyl-6-methoxybenzamide (0.593 g, 46%) as a solid. $^1$H NMR (400 MHz, CHLOROFORM-d) δ 3.81 (s, 3H), 4.62 (s, 1H), 4.63 (s, 1H), 6.07 (vb.s, 2H), 6.19 (d, J=8.2 Hz, 1H), 6.32 (d, J=8.2

Hz, 1H), 7.07 (t, J=8.2 Hz, 1H), 7.14-7.54 (m, 5H), 8.05 (br. s., 1H); HPLC: $t_R$=4.72 min, $UV_{254}$=99%; HRMS (ESI): m/z calcd for $C_{15}H_{16}N_2O_2$ [M+1]$^+$ 257.1296. found 257.1294.

2-Amino-N-benzyl-6-hydroxybenzamide

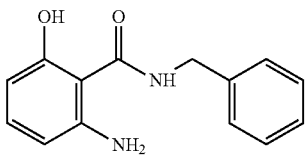 [SMILES: Nc1cccc(O)c1C(=O)NCc1ccccc1]

To a solution of 2-amino-N-benzyl-6-methoxybenzamide (0.228 g, 0.89 mmol, 1.0 equiv) in 3 mL of anhydrous DMF was added 1-dodecanethiol (0.360 g, 1.78 mmol, 2.0 equiv), followed by adding NaOMe (0.385 g of 25% solution in MeOH, 1.78, 2.0 equiv). The mixture was heated in a microwave at 150° C. for 10 min. The mixture passed through a silica gel plug, which was washed with an ethyl acetate-methanol mixture (1:1). The crude product was purified by PL-SO$_3$H MP SPE (Varian) to give 2-Amino-N-benzyl-6-hydroxybenzamide (0.176 g, 82%) as thick oil. $^1$H NMR (400 MHz, CHLOROFORM-d) δ 3.55-4.20 (vb.s., 2H), 4.60 (s, 1H), 4.61 (s, 1H), 6.25 (d, J=7.8 Hz, 1H), 6.50 (d, J=8.2 Hz, 1H), 7.09 (t, J=8.0 Hz, 1H), 7.16-7.52 (m, 5H), 8.58 (br. s., 1H), 12.05 (br. s., 1H); HPLC: $t_R$=3.97 min, $UV_{254}$=98%; HRMS (ESI): m/z calcd for $C_{14}H_{14}N_2O_2$ [M+1]$^+$ 243.11. found 243.1134.

General procedure for the syntheses of 2,3-dihydroquinazolin-4-ones and quinazolin-4-ones To a solution of 3-(chloromethyl)-4-methoxybenzaldehyde (300 umol, 1.0 equiv) and the appropriately substituted phenol or thiolphenol (360 umol, 1.2 equiv) in 1.5 mL of anhydrous DMA was added K$_2$CO$_3$ (1.5 mmol, 5 equiv). The mixture was heated in a microwave at 150° C. for 10 min. The solid was filtered. To the clear solution was added 2-aminobenzamides (1.2 equiv), followed by Ytterbium trifluoromethanesulfonate (150 umol, 0.5 equiv). The mixture was heated in a microwave at 200° C. for 10 min giving the desired 2,3-dihydroquinazolin-4-ones. Adding a DDQ (300 umol, 1.5 M in acetonitrile, 1.0 equiv) solution to the reaction mixture containing 2,3-dihydroquinazolin-4-ones and stirring the resulted mixture for 1 hour gave quinazolin-4-ones. All crude products were purified by HPLC. PL-HCO$_3$ MP SPE was used to remove TFA. The final products were obtained as solids in 20-50% yields.

N-(4-(5-(3-(Furan-2-ylmethyl)-4-oxo-1,2,3,4-tetrahydroquinazolin-2-yl)-2-methoxybenzyloxy)phenyl)acetamide (Compound 3)

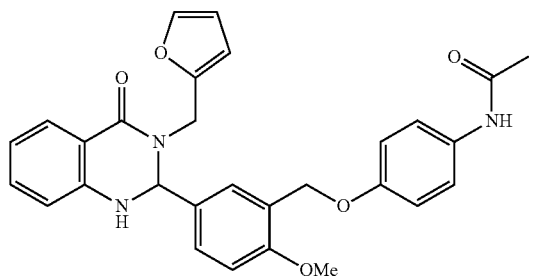 [SMILES: COc1ccc(C2Nc3ccccc3C(=O)N2Cc2ccco2)cc1COc1ccc(NC(C)=O)cc1]

$^1$H NMR (400 MHz, CHLOROFORM-d) δ 2.11 (s, 3H), 3.72 (d, J=15.6 Hz, 1H), 3.83 (s, 3H), 4.25 (v.b.s., 1H), 5.01 (s, 2H), 5.26 (d, J=15.6 Hz, 1H), 5.71 (s, 1H), 6.03-6.29 (m, 2H), 6.48 (d, J=7.8 Hz, 1H), 6.83 (dd, J=18.2, 8.8 Hz, 3H), 7.10-7.61 (m, 7H), 7.92 (d, J=7.0 Hz, 1H); HPLC: $t_R$=5.40 min, $UV_{254}$=91%; HRMS (ESI): m/z calcd for $C_{29}H_{27}N_3O_5$ [M+1]$^+$ 498.2029. found 498.2025.

N-(4-(5-(3-Benzyl-4-oxo-1,2,3,4-tetrahydroquinazolin-2-yl)-2-methoxybenzyloxy)phenyl)acetamide (Compound 3/2)

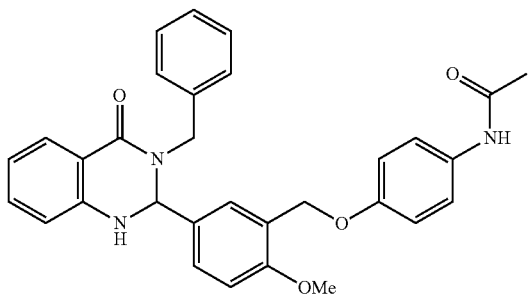

$^1$H NMR (400 MHz, CHLOROFORM-d) δ 2.12 (s, 3H), 3.66 (d, J=15.3 Hz, 1H), 3.83 (s, 3H), 5.00 (s, 2H), 5.48 (d, J=15.3 Hz, 1H), 5.57 (s, 1H), 6.49 (d, J=7.8 Hz, 1H), 6.67-7.00 (m, 4H), 7.05-7.57 (m, 11H), 7.99 (d, J=7.8 Hz, 1H); HPLC: $t_R$=5.69 min, $UV_{254}$=98%; HRMS (ESI): m/z calcd for $C_{31}H_{29}N_3O_4$ [M+1]$^+$ 508.2242. found 508.2233.

N-(4-(5-(3-Benzyl-4-oxo-1,2,3,4-tetrahydroquinazolin-2-yl)-2-methoxybenzylthio)phenyl)acetamide (Compound 3/5)

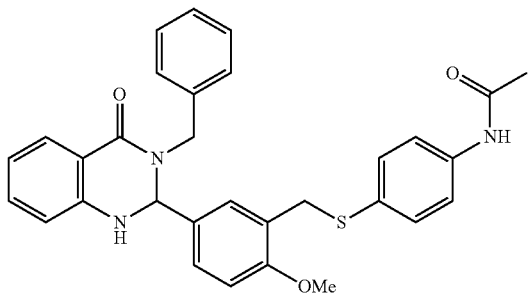 [SMILES: COc1ccc(C2Nc3ccccc3C(=O)N2Cc2ccccc2)cc1COc1ccc(NC(C)=O)cc1]

$^1$H NMR (400 MHz, CHLOROFORM-d) δ 2.14 (s, 3H), 3.50 (d, J=15.4 Hz, 1H), 3.83 (s, 3H), 3.88 (d, J=13.1 Hz, 1H), 4.00 (d, J=13.1 Hz, 1H), 5.42 (d, J=15.3 Hz, 1H), 5.45 (s, 1H), 6.52 (d, J=8.2 Hz, 1H), 6.74 (d, J=8.6 Hz, 1H), 6.79 (d, J=2.0 Hz, 1H), 6.84 (t, J=7.4 Hz, 1H), 7.06 (dd, J=8.4, 2.2 Hz, 1H), 7.10-7.33 (m, 9H), 7.37 (d, J=8.6 Hz, 2H), 7.68 (br. s., 1H), 7.96 (d, J=6.6 Hz, 1H); HPLC: $t_R$=5.97 min, $UV_{254}$=98%; HRMS (ESI): m/z calcd for $C_{31}H_{29}N_3O_3S$ [M+1]$^+$ 524.2002. found 524.2002.

N-(4-(5-(3-Benzyl-5-hydroxy-4-oxo-1,2,3,4-tetrahydroquinazolin-2-yl)-2-methoxybenzyloxy)phenyl)acetamide (Compound 3/4)

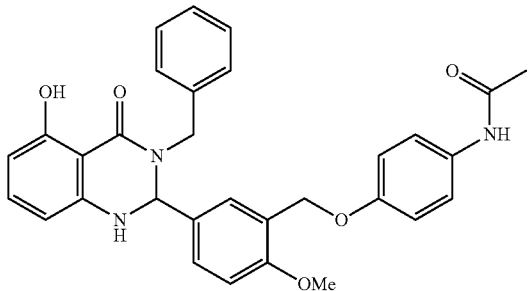 [SMILES: COc1ccc(C2Nc3cccc(O)c3C(=O)N2Cc2ccccc2)cc1COc1ccc(NC(C)=O)cc1]

$^1$H NMR (400 MHz, CHLOROFORM-d) δ 2.16 (s, 3H), 3.67 (d, J=15.5 Hz, 1H), 3.87 (s, 3H), 4.38 (bs, 1H), 5.05 (s, 2H), 5.37 (d, J=15.2 Hz, 1H), 5.58 (d, J=1.6 Hz, 1H), 5.95 (dd, J=8.0, 1.0 Hz, 1H), 6.35 (dd, J=8.4, 0.9 Hz, 1H), 6.80-6.92 (m, 3H), 7.09-7.40 (m, 10H), 12.34 (s., 1H); HPLC: $t_R$=6.11 min, $UV_{254}$=96%; HRMS (ESI): m/z calcd for $C_{31}H_{29}N_3O_5$ [M+1]$^+$ 524.2185. found 524.2184.

N-(4-(5-(3-(Furan-2-ylmethyl)-4-oxo-3,4-dihydroquinazolin-2-yl)-2-methoxybenzyloxy)phenyl)acetamide (Compound 3/1)

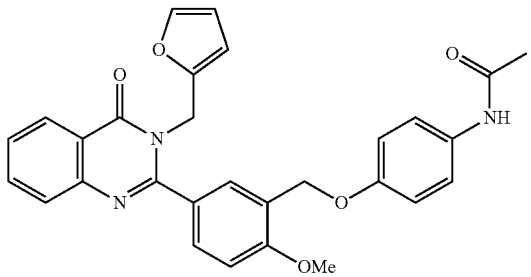 [SMILES: COc1ccc(-c2nc3ccccc3c(=O)n2Cc2ccco2)cc1COc1ccc(NC(C)=O)cc1]

$^1$H NMR (400 MHz, CHLOROFORM-d) δ 2.15 (s, 3H), 3.95 (s, 3H), 5.12 (s, 2H), 5.19 (s, 2H), 6.12 (d, J=2.7 Hz, 1H), 6.22-6.28 (m, 1H), 6.93 (d, J=9.0 Hz, 2H), 7.00 (d, J=8.6 Hz, 1H), 7.12 (br. s., 1H), 7.24 (s, 1H), 7.39 (d, J=9.0 Hz, 2H), 7.46-7.56 (m, 2H), 7.64-7.82 (m, 3H), 8.33 (d, J=8.2 Hz, 1H); HPLC: $t_R$=5.49 min, $UV_{254}$=95%; HRMS (ESI): m/z calcd for $C_{29}H_{25}N_3O_5$ [M+1]$^+$ 496.1872. found 496.1873.

N-(4-(5-(3-Benzyl-4-oxo-3,4-dihydroquinazolin-2-yl)-2-methoxybenzyloxy)phenyl)acetamide (Compound 3/3)

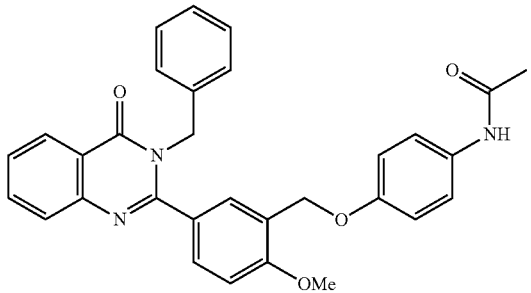 [SMILES: COc1ccc(-c2nc3ccccc3c(=O)n2Cc2ccccc2)cc1COc1ccc(NC(C)=O)cc1]

$^1$H NMR (400 MHz, CHLOROFORM-d) δ 2.13 (s, 3H), 3.91 (s, 3H), 5.04 (s, 2H), 5.26 (s, 2H), 6.81-7.04 (m, 5H), 7.11-7.26 (m, 4H), 7.38 (d, J=9.0 Hz, 2H), 7.46-7.58 (m, 2H), 7.71-7.83 (m, 2H), 8.36 (d, J=7.8 Hz, 1H); HPLC: $t_R$=5.73 min, $UV_{254}$=98%; HRMS (ESI): m/z calcd for $C_{31}H_{27}N_3O_4$ [M+1]$^+$ 506.2086. found 506.2082.

Generation of Stable Cell-Lines Expressing TSHR, LHCGR or FSHR.

cDNA for human TSHR was amplified by PCR from hTSHR-pSVL (1) and inserted into the pcDNA3.1(−)/hygromycin vector using restriction sites XhoI and BamHI. cDNA for human LHCGR was amplified by PCR from hLHR-pGS5 (2) and was inserted into the pcDNA3.1(+)/hygromycin vector using restriction sites BamHI and XhoI. The FSHR cDNA in pcDNA3.1 was obtained from the Missouri S&T cDNA Resource Center (www.cDNA.org) and was subcloned into the pcDNA3.1(−)/hygromycin vector. Constructs were confirmed by sequencing (MWG Biotech).

HEK-EM 293 cells were transfected with the cDNA of TSHR, LHCGR or FSHR using FuGENE 6 Transfection reagent (Roche Diagnostics) according to the manufacturer's protocol. Two days after transfection cells were passaged and grown in Dulbecco's modified Eagle's Medium (DMEM) supplemented with 10% fetal bovine serum, 100 units/ml penicillin and 10 μg/ml streptomycin (Life Technologies Inc.) and with hygromycin (250 μg/ml) as a selection marker. After 7 to 10 days hygromycin-resistant clones were selected, and after a few days of further growth submitted for a cAMP assay to identify clones that stably express the appropriate receptor.

Cell Culture.

Cells stably expressing TSHR, LHCGR or FSHR and parental HEK 293 cells were maintained in DMEM medium containing 10% FBS, 100 units/ml Penicillin, 100 μg/ml Streptomycin, at 37° C. in 5% $CO_2$. For the cells lines stably expressing TSHR, LHCGR or FSHR, additional 250 μg/ml Hygromycin was added during the cell culture. The cells were seeded at a density of 3 to 4 million cells in a T175 flask containing 35 ml of media and were allowed to grow for 3 days to reach 80-90% confluence. A flask of HEK 293 cells at this density generally yielded 30 million cells total.

Homogeneous Time Resolved Fluorescence (HTRF) cAMP Assay.

Compounds were assayed using a HTRF cAMP detection kit (Cisbio, Bedford, Mass.) on both TSHR cell line and parental cell line. Briefly, 750 cells were plated in 2.5 μl/well of complete media (DMEM containing 10% FCS) in 1536 well solid bottom white plates and 20 nl/well compound in DMSO solution or controls was added. Following 30 minute incubation at room temperature, 2.5 μl/well of labeled d2 cAMP and 2.5 μl/well of anti-cAMP antibody (both diluted 1:20 in lysis buffer) were added to each well using a flying reagent dispenser (Aurora Discovery, San Diego). Plates were measured using the Envision plate reader (PerkinElmer, Boston, Mass.) with excitation at 330 nm and emissions of 615 nm and 660 nm.

Compound Preparation.

Compounds were serially diluted 1:5 or 1:2.236 in DMSO in 384-well plates to yield seven or fifteen concentrations (minimally 10 mM, 2 mM, 0.4 mM, 80 μM, 16 μM, 3.2 μM and 0.64 μM) and formatted into 1,536-well plates at 7 μl/well. Final compound concentrations during cell incubation ranged from 1.60 nM to 25.0 μM.

Data Analysis.

The maximal response (100% activity) was determined by the response of 30 mU/ml TSH and the basal response (0% activity) was measured by the DMSO control in the TSH screen. The $EC_{50}$ values of compounds were calculated from the concentration-response curves by nonlinear regression analysis using Prism software (GraphPad Software, San Diego, Calif.).

Confirmatory cAMP Assay and Test for Selectivity Towards TSHR 50,000 cells/well were plated in complete media (DMEM containing 10% FCS) in 96 well plates. Cells were cultured for 24 h before incubation for 1 h in serum-free DMEM containing 1 mM 3-isobutyl-1-methylxanthine (IBMX) (SIGMA) and bovine TSH (1.8 µM) or human LH or FSH (1000 ng/ml) or compounds (0.01 µM-100 µM) in a humidified 5% $CO_2$ incubator at 37 C. Following aspiration of the medium after incubation with compounds, cells were lysed using lysis buffer of the cAMP-Screen Direct System (Applied Biosystems, Cat #CSD200). The cAMP content of the cell lysate was determined using the manufacturer's protocol. The potency ($EC_{50}$) was obtained from dose response curves (0-100 µM compound) by data analysis with GraphPad Prism 4 for Windows.

Below is a List of Compounds that were Assayed Via the Homogeneous Time Resolved Fluorescence (HTRF) cAMP Assay.

| Structure | AC50 (µM) | Log AC50 | Maximum Activity compared to TSH |
|---|---|---|---|
| 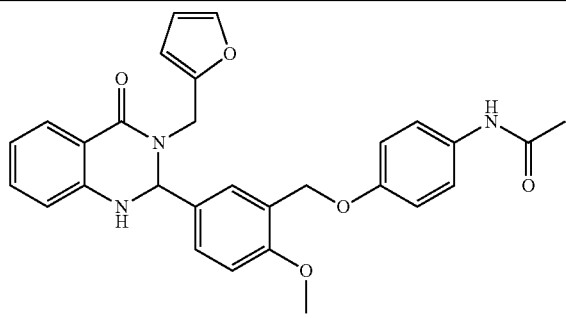<br>Structure 1 | 12.59 | −4.90 | 159.24 |
| 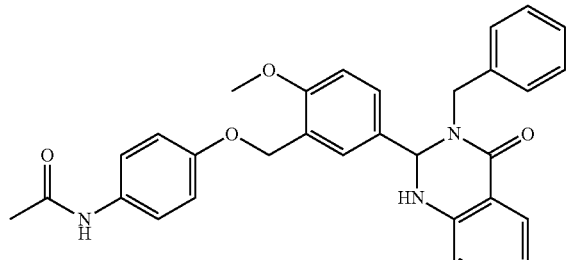<br>Structure 2 | 11.22 | −4.95 | 217.29 |
| 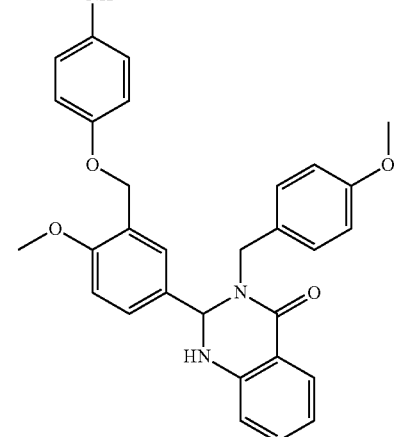<br>Structure 3 | 4.47 | −5.35 | 93.95 |

-continued

| Structure | AC50 (μM) | Log AC50 | Maximum Activity compared to TSH |
|---|---|---|---|
| Structure 4 | 7.08 | −5.15 | 171.91 |
| Structure 5 | 15.85 | −4.80 | 174.77 |
| Structure 6 | 17.78 | −4.75 | 180.81 |
| Structure 7 | 8.91 | −5.05 | 152.47 |

| Structure | AC50 (μM) | Log AC50 | Maximum Activity compared to TSH |
|---|---|---|---|
| 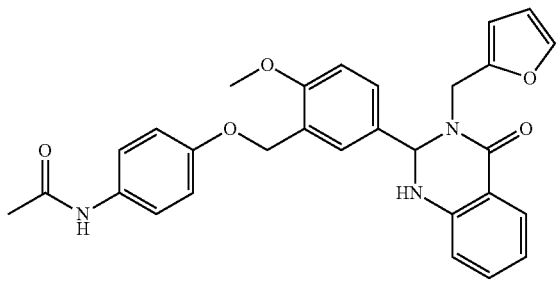<br>Structure 8 | 14.13 | −4.85 | 115.96 |
| 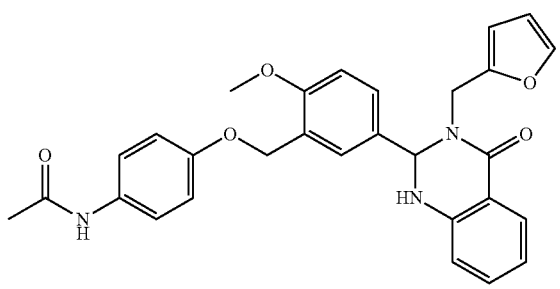<br>Structure 9 | 17.78 | −4.75 | 115.62 |
| 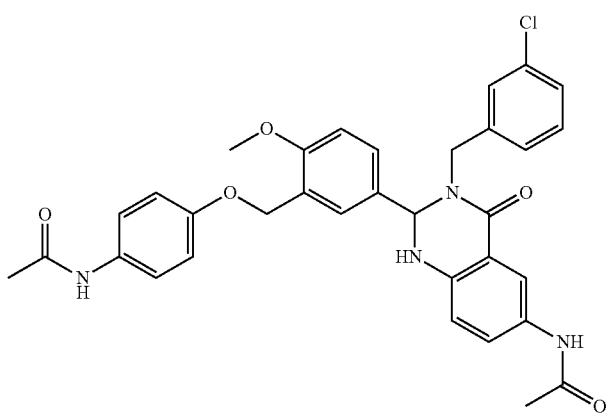<br>Structure 10 | 7.94 | −5.10 | 122.44 |

-continued
| Structure | AC50 (μM) | Log AC50 | Maximum Activity compared to TSH |
|---|---|---|---|
| 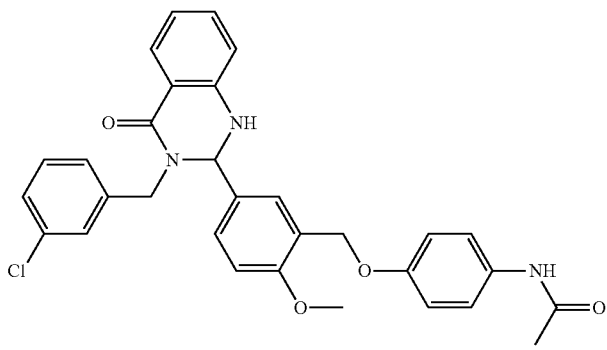<br>Structure 11 | 3.16 | −5.50 | 113.94 |
| 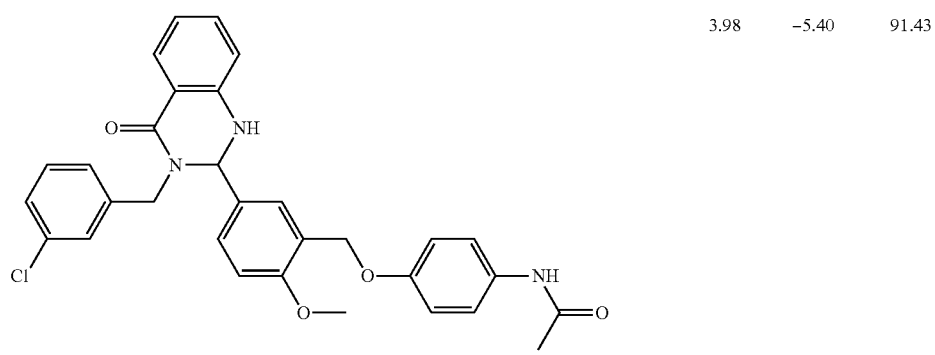<br>Structure 12 | 3.98 | −5.40 | 91.43 |
| 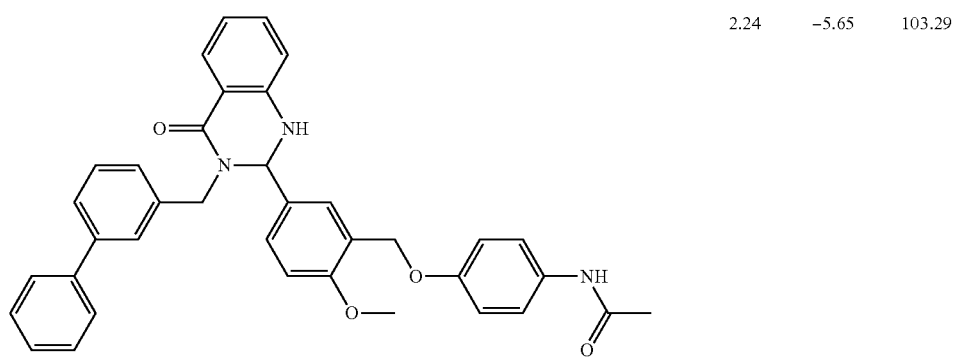<br>Structure 13 | 2.24 | −5.65 | 103.29 |

-continued
| Structure | AC50 (μM) | Log AC50 | Maximum Activity compared to TSH |
|---|---|---|---|
| 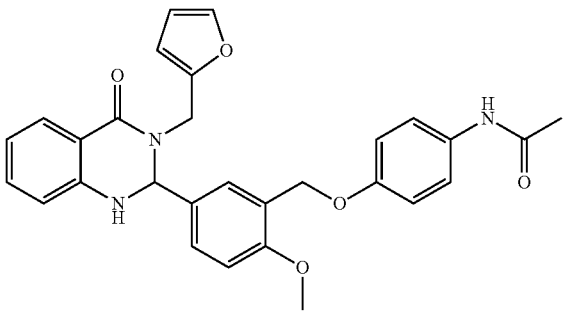<br>Structure 14 | 11.22 | −4.95 | 104.66 |
| 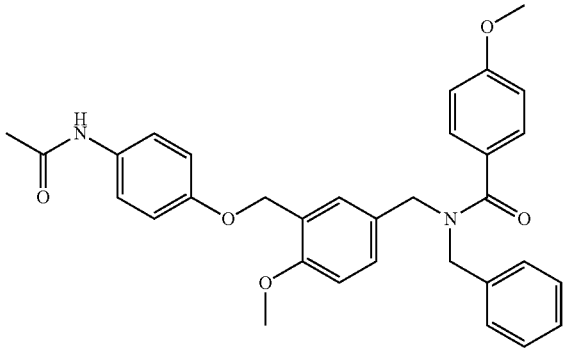<br>Structure 15 | 12.59 | −4.90 | 123.21 |
| 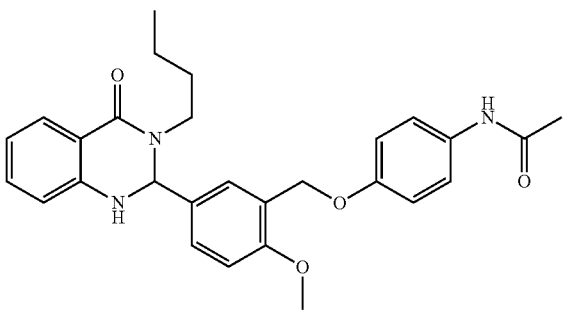<br>Structure 16 | 19.95 | −4.70 | 97.95 |
| 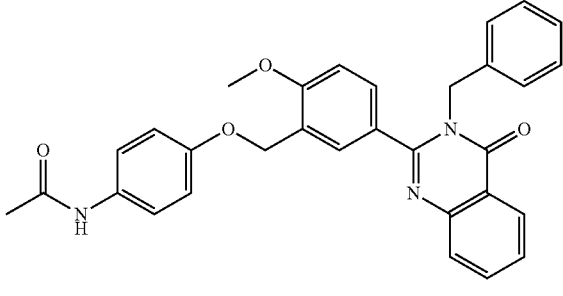<br>Structure 17 | 10.00 | −5.00 | 93.46 |

| Structure | AC50 (μM) | Log AC50 | Maximum Activity compared to TSH |
|---|---|---|---|
| 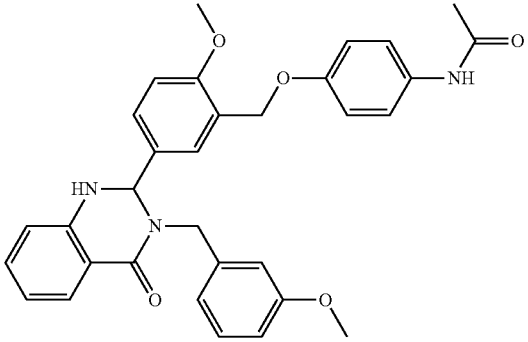<br>Structure 18 | 6.31 | −5.20 | 215.89 |
| 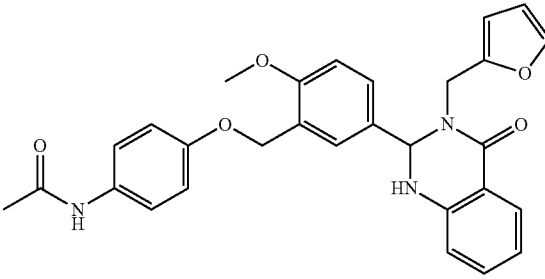<br>Structure 19 | 15.85 | −4.80 | 142.18 |
| 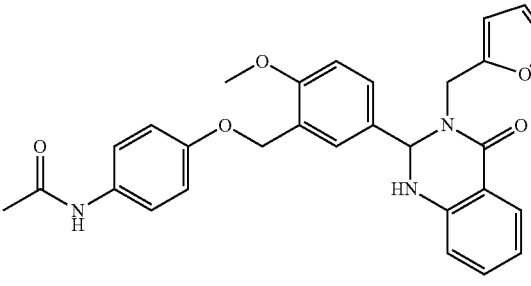<br>Structure 20 | 14.13 | −4.85 | 156.28 |
| 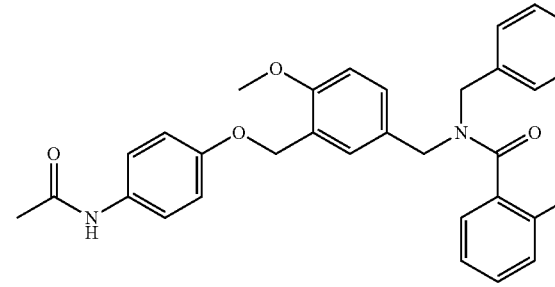<br>Structure 21 | 25.12 | −4.60 | 236.35 |

-continued
| Structure | AC50 (μM) | Log AC50 | Maximum Activity compared to TSH |
|---|---|---|---|
| 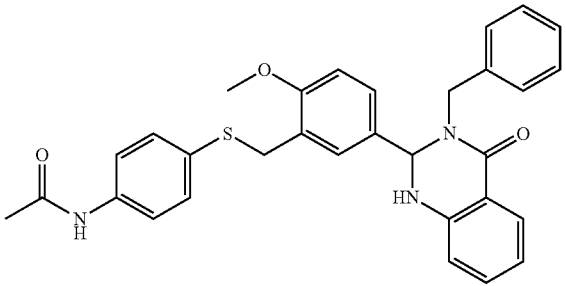<br>Structure 22 | 7.94 | −5.10 | 463.89 |
| 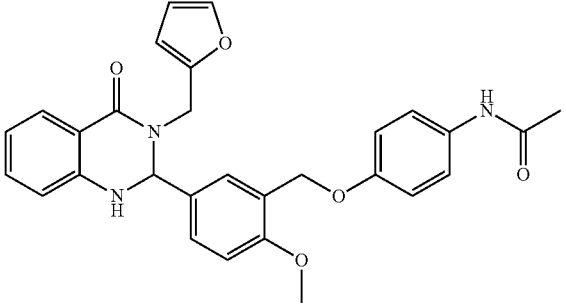<br>Structure 23 | 15.85 | −4.80 | 165.50 |
| 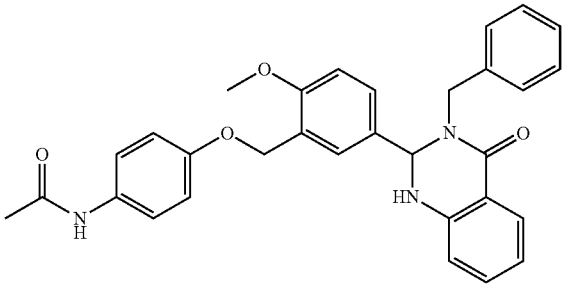<br>Structure 24 | 7.08 | −5.15 | 159.76 |
| 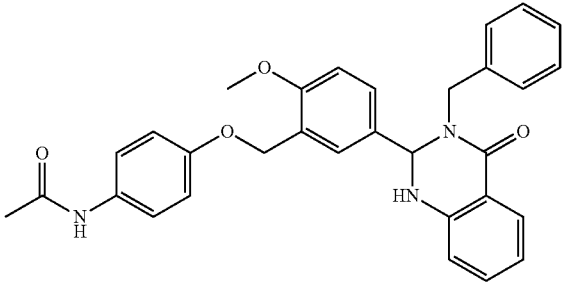<br>Structure 25 | 8.91 | −5.05 | 207.56 |

-continued
| Structure | AC50 (μM) | Log AC50 | Maximum Activity compared to TSH |
|---|---|---|---|
| 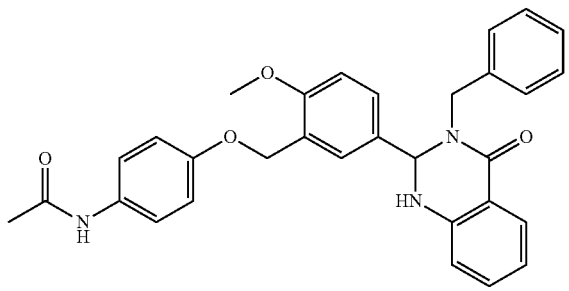<br>Structure 26 | 10.00 | −5.00 | 217.05 |
| 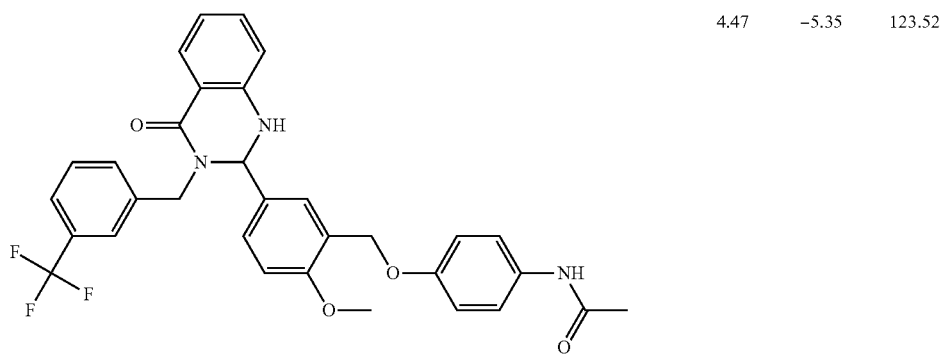<br>Structure 27 | 4.47 | −5.35 | 123.52 |
| 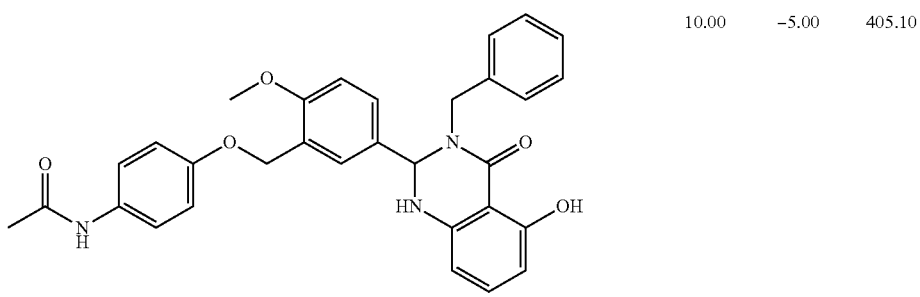<br>Structure 28 | 10.00 | −5.00 | 405.10 |
| 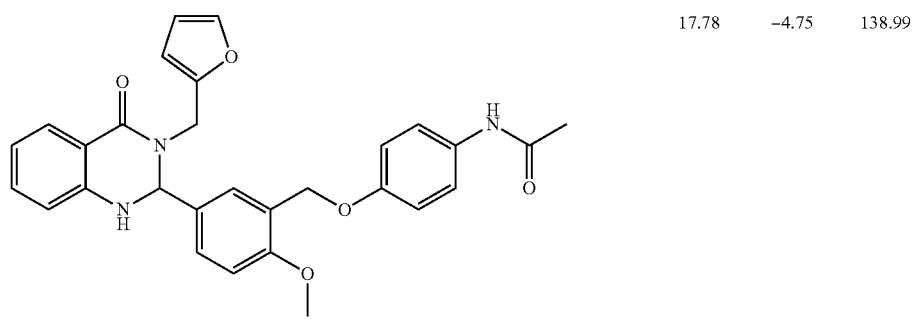<br>Structure 29 | 17.78 | −4.75 | 138.99 |

-continued
| Structure | AC50 (μM) | Log AC50 | Maximum Activity compared to TSH |
|---|---|---|---|
| 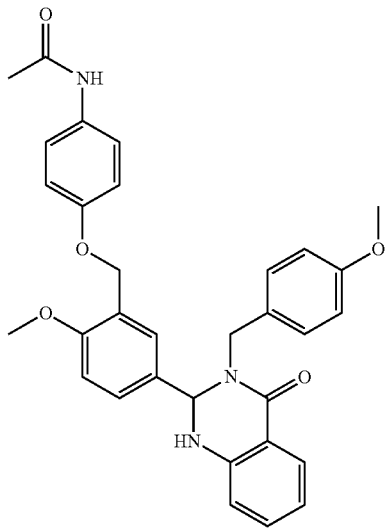 Structure 30 | 3.16 | −5.50 | 63.65 |
| 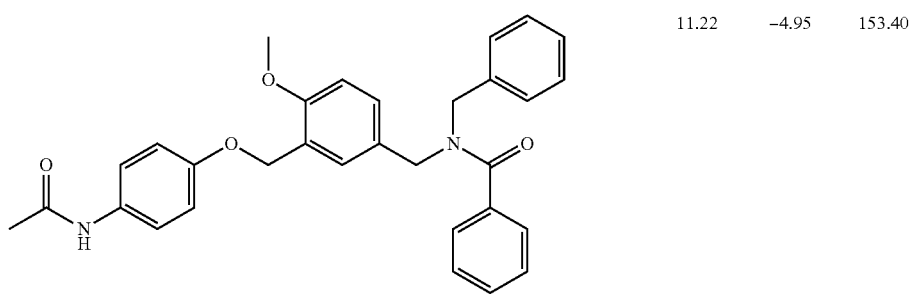 Structure 31 | 11.22 | −4.95 | 153.40 |
| 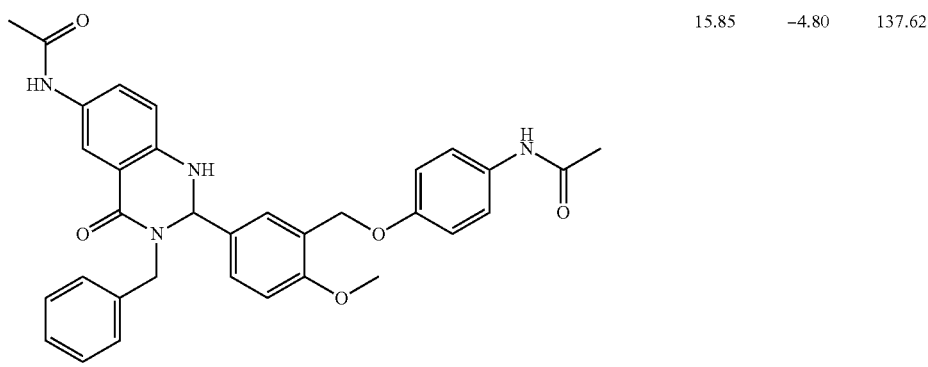 Structure 32 | 15.85 | −4.80 | 137.62 |

-continued
| Structure | AC50 (μM) | Log AC50 | Maximum Activity compared to TSH |
|---|---|---|---|
| 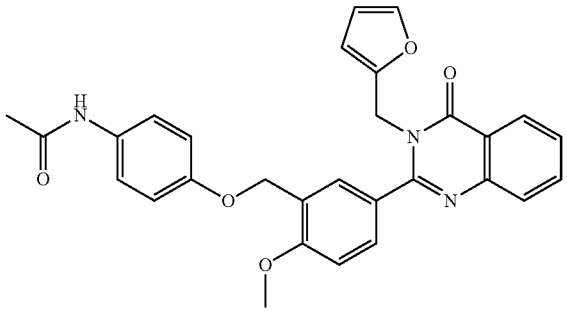<br>Structure 33 | 17.78 | −4.75 | 168.66 |
| 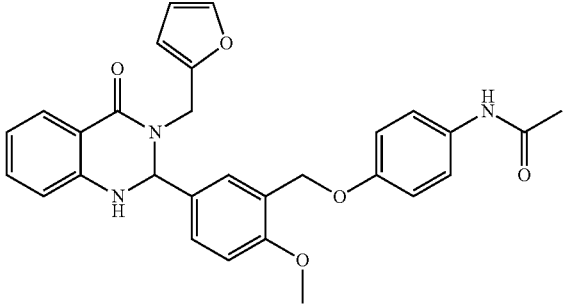<br>Structure 34 | 15.85 | −4.80 | 122.30 |
| 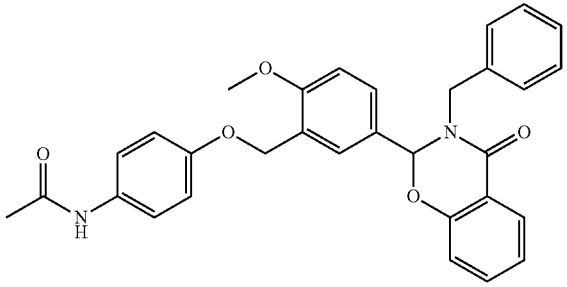<br>Structure 35 | 12.59 | −4.90 | 115.01 |

-continued
| Structure | AC50 (μM) | Log AC50 | Maximum Activity compared to TSH |
|---|---|---|---|
| 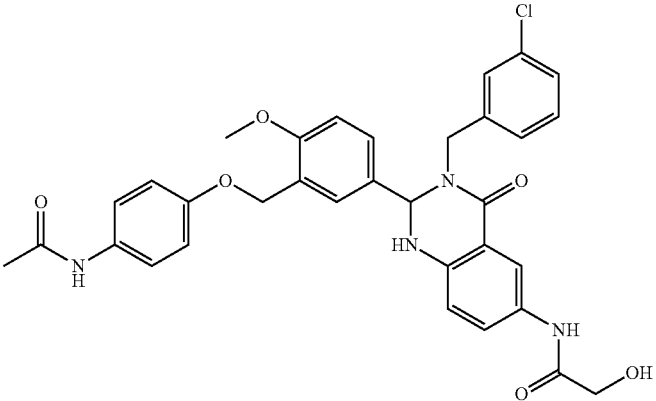<br>Structure 36 | 5.62 | −5.25 | 115.47 |
| 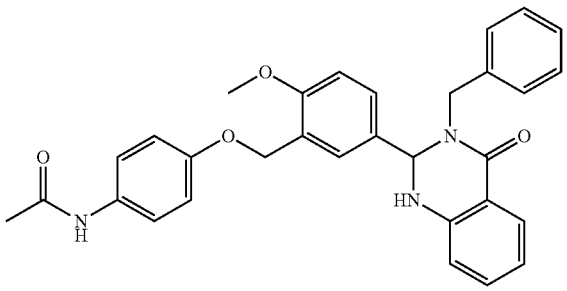<br>Structure 37 | 8.91 | −5.05 | 104.22 |
| 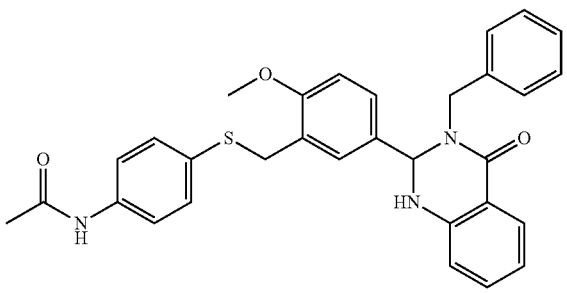<br>Structure 38 | 7.08 | −5.15 | 573.36 |
| 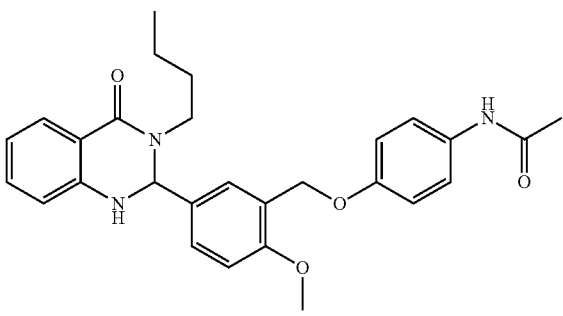<br>Structure 39 | 19.95 | −4.70 | 123.60 |

-continued
| Structure | AC50 (μM) | Log AC50 | Maximum Activity compared to TSH |
|---|---|---|---|
| 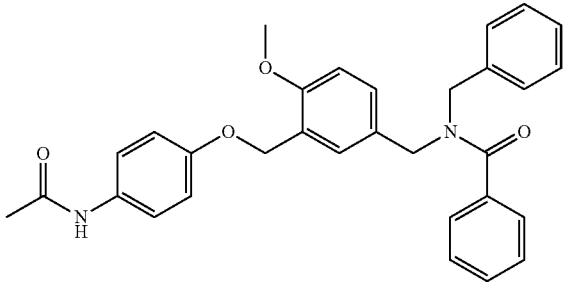<br>Structure 40 | 11.22 | −4.95 | 128.80 |
| 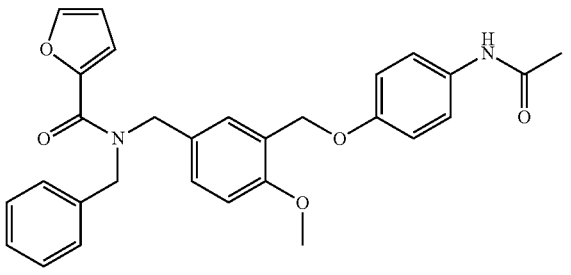<br>Structure 41 | 15.85 | −4.80 | 122.50 |
| 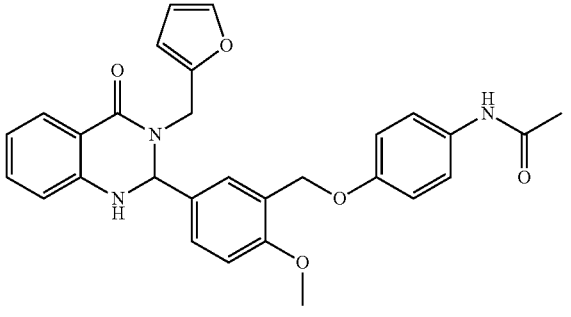<br>Structure 42 | 14.13 | −4.85 | 131.51 |
| 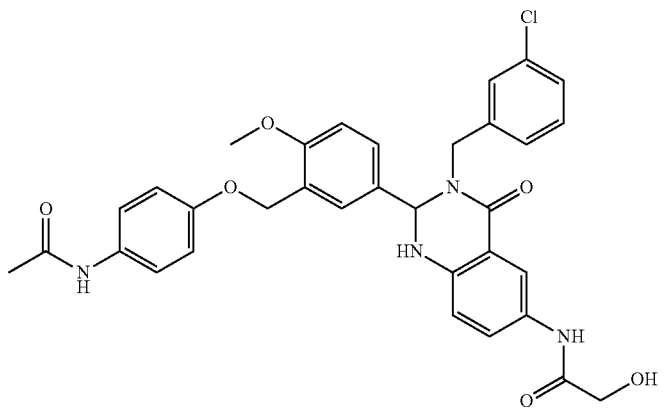<br>Structure 43 | 10.00 | −5.00 | 128.45 |

| Structure | AC50 (μM) | Log AC50 | Maximum Activity compared to TSH |
|---|---|---|---|
| 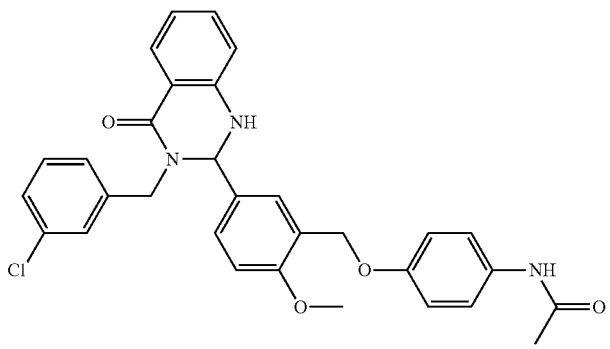<br>Structure 44 | 7.08 | −5.15 | 105.58 |
| 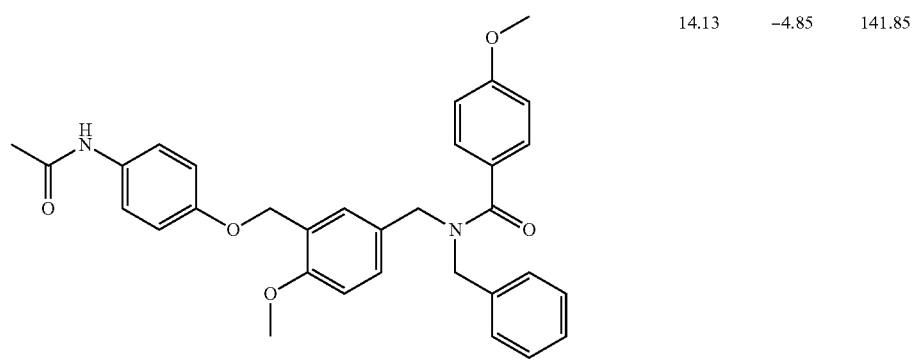<br>Structure 45 | 14.13 | −4.85 | 141.85 |
| 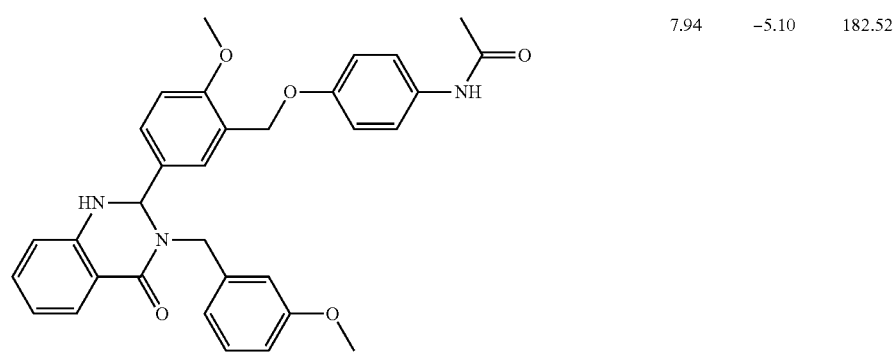<br>Structure 46 | 7.94 | −5.10 | 182.52 |

-continued
| Structure | AC50 (μM) | Log AC50 | Maximum Activity compared to TSH |
|---|---|---|---|
| 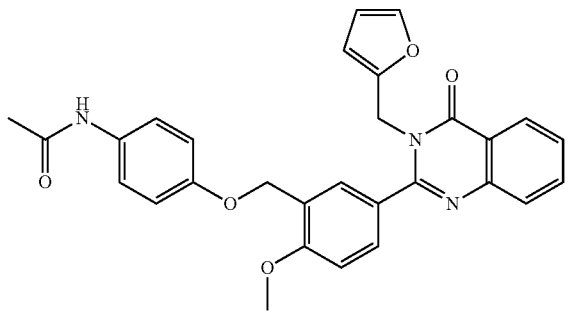<br>Structure 47 | 25.12 | −4.60 | 165.16 |
| 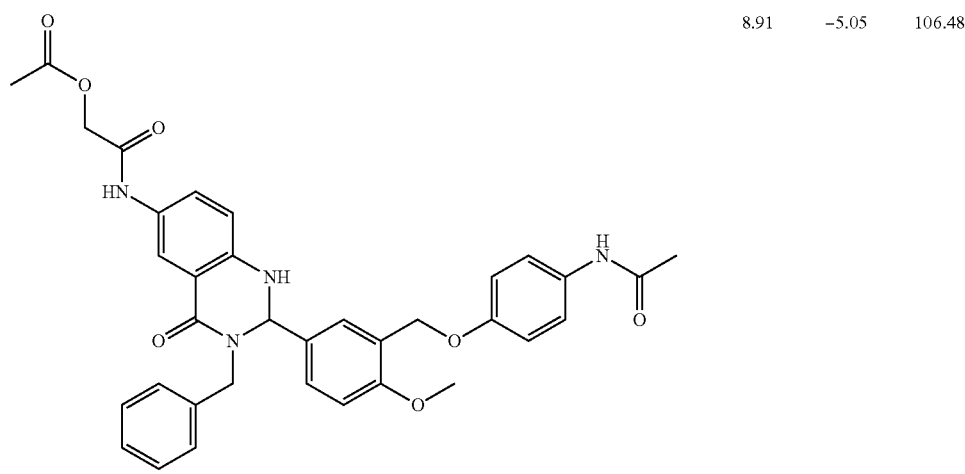<br>Structure 48 | 8.91 | −5.05 | 106.48 |
| 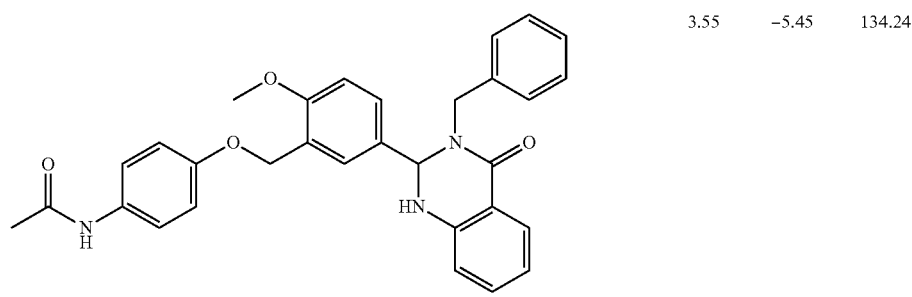<br>Structure 49 | 3.55 | −5.45 | 134.24 |

-continued

| Structure | AC50 (μM) | Log AC50 | Maximum Activity compared to TSH |
|---|---|---|---|
| Structure 50 | 2.82 | −5.55 | 70.37 |
| Structure 51 | 15.85 | −4.80 | 174.87 |
| Structure 52 | 8.91 | −5.05 | 104.78 |
| Structure 53 | 12.59 | −4.90 | 141.76 |

-continued

| Structure | AC50 (μM) | Log AC50 | Maximum Activity compared to TSH |
|---|---|---|---|
| Structure 54 | 10.00 | −5.00 | 115.69 |
| Structure 55 | 7.94 | −5.10 | 194.91 |
| Structure 56 | 11.22 | −4.95 | 110.90 |
| Structure 57 | 14.13 | −4.85 | 100.67 |

-continued

| Structure | AC50 (μM) | Log AC50 | Maximum Activity compared to TSH |
|---|---|---|---|
| Structure 58 | 8.91 | −5.05 | 93.09 |
| Structure 59 | 17.78 | −4.75 | 226.43 |
| Structure 60 | 6.31 | −5.20 | 189.97 |
| Structure 61 | 7.94 | −5.10 | 302.11 |

-continued

| Structure | AC50 (μM) | Log AC50 | Maximum Activity compared to TSH |
|---|---|---|---|
| Structure 62 | 7.08 | −5.15 | 241.92 |
| Structure 63 | 5.01 | −5.30 | 166.46 |
| Structure 64 | 7.94 | −5.10 | 70.53 |
| Structure 65 | 14.13 | −4.85 | 51.63 |

-continued
| Structure | AC50 (μM) | Log AC50 | Maximum Activity compared to TSH |
|---|---|---|---|
| 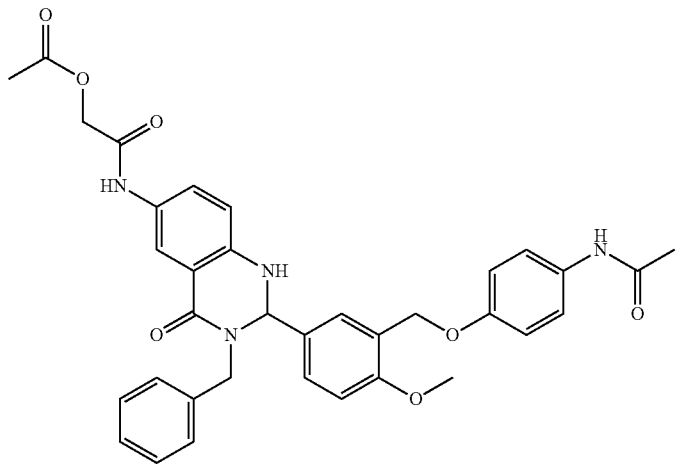<br>Structure 66 | 8.91 | −5.05 | 64.52 |
| 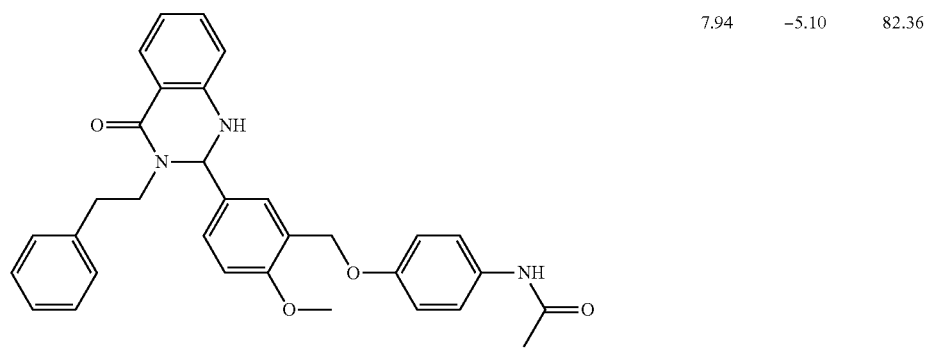<br>Structure 67 | 7.94 | −5.10 | 82.36 |
| 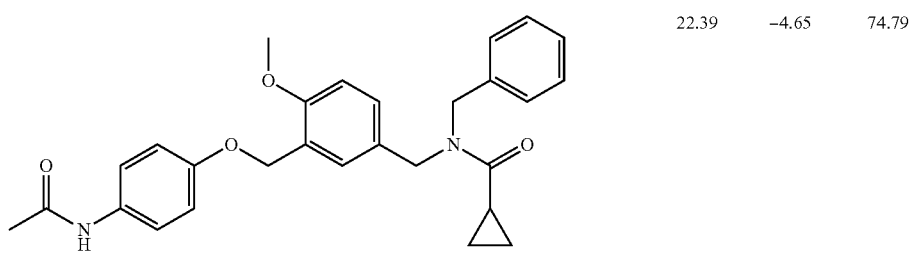<br>Structure 68 | 22.39 | −4.65 | 74.79 |

-continued

| Structure | AC50 (μM) | Log AC50 | Maximum Activity compared to TSH |
|---|---|---|---|
| Structure 69 | 25.12 | −4.60 | 44.83 |
| Structure 70 | 10.00 | −5.00 | 53.96 |
| Structure 71 | 7.94 | −5.10 | 44.19 |
| Structure 72 | 3.98 | −5.40 | 55.25 |

-continued
| Structure | AC50 (μM) | Log AC50 | Maximum Activity compared to TSH |
|---|---|---|---|
| 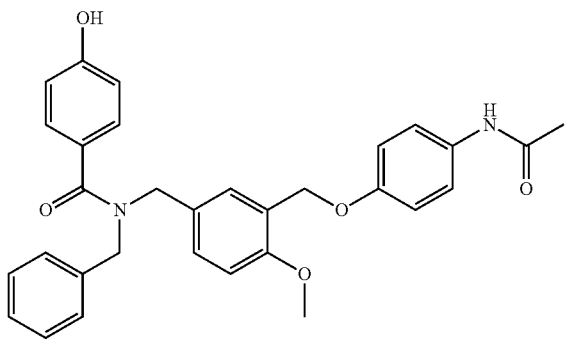<br>Structure 73 | 28.18 | −4.55 | 75.04 |
| 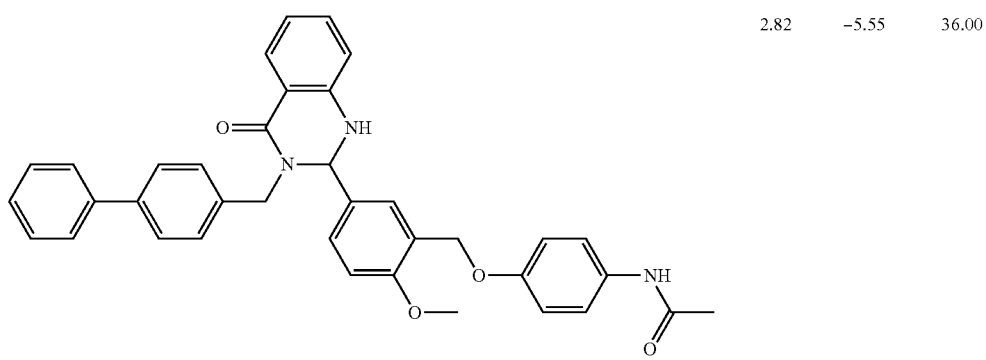<br>Structure 74 | 2.82 | −5.55 | 36.00 |
| 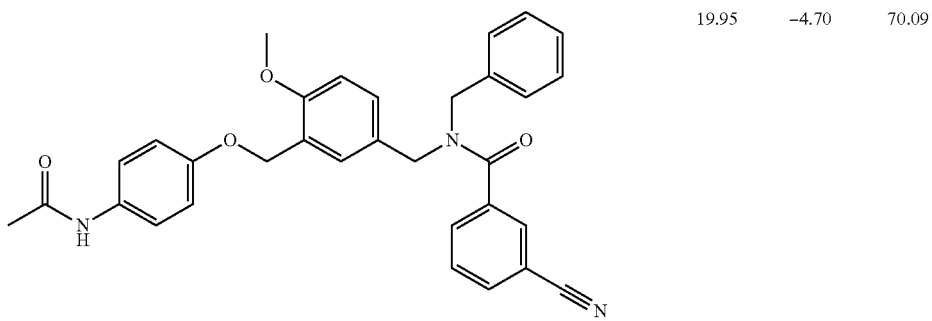<br>Structure 75 | 19.95 | −4.70 | 70.09 |

-continued
| Structure | AC50 (μM) | Log AC50 | Maximum Activity compared to TSH |
|---|---|---|---|
| 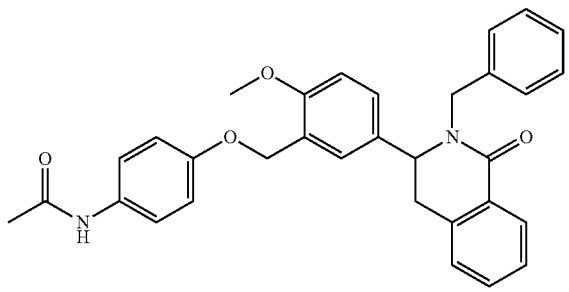<br>Structure 76 | 6.31 | −5.20 | 64.77 |
| 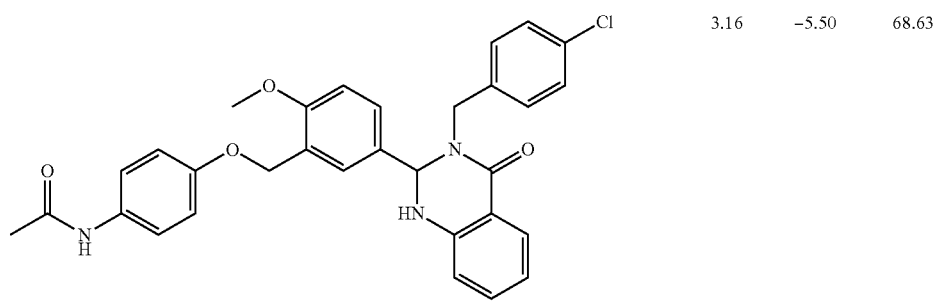<br>Structure 77 | 3.16 | −5.50 | 68.63 |
| 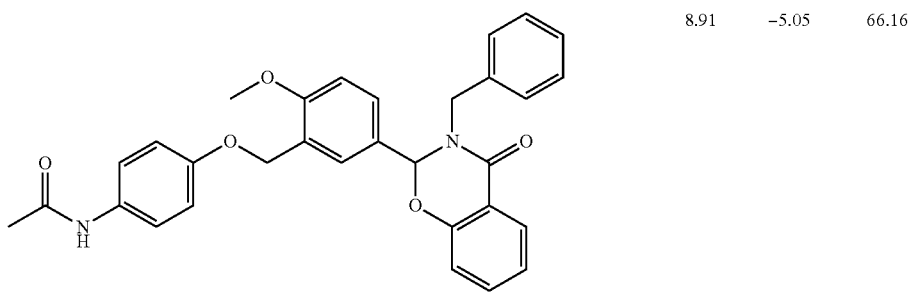<br>Structure 78 | 8.91 | −5.05 | 66.16 |

-continued
| Structure | AC50 (μM) | Log AC50 | Maximum Activity compared to TSH |
|---|---|---|---|
| Structure 79 | 1.78 | −5.75 | 61.52 |
| Structure 80 | 22.39 | −4.65 | 40.00 |
| Structure 81 | 15.85 | −4.80 | 76.98 |
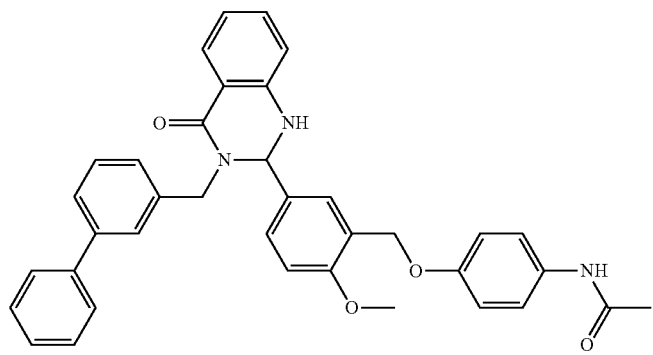

-continued
| Structure | AC50 (μM) | Log AC50 | Maximum Activity compared to TSH |
|---|---|---|---|
| 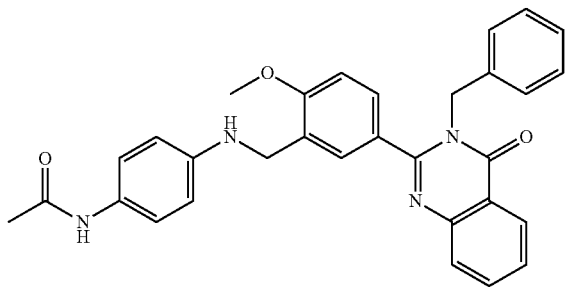 Structure 82 | 25.12 | −4.60 | 58.96 |
| 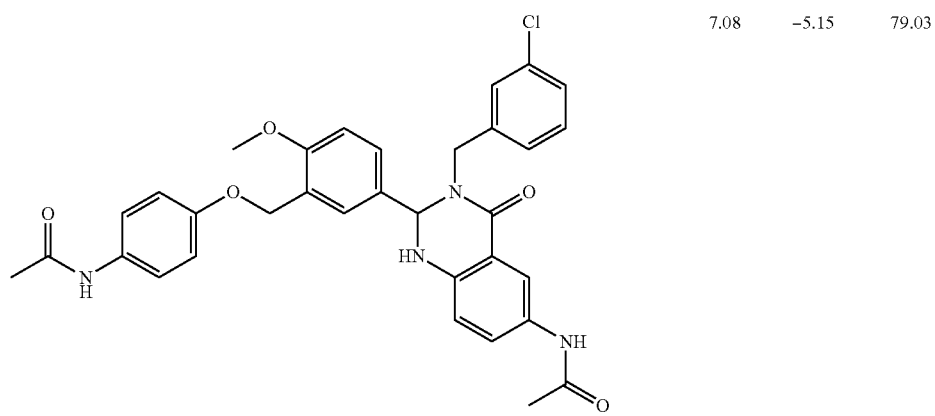 Structure 83 | 7.08 | −5.15 | 79.03 |
| 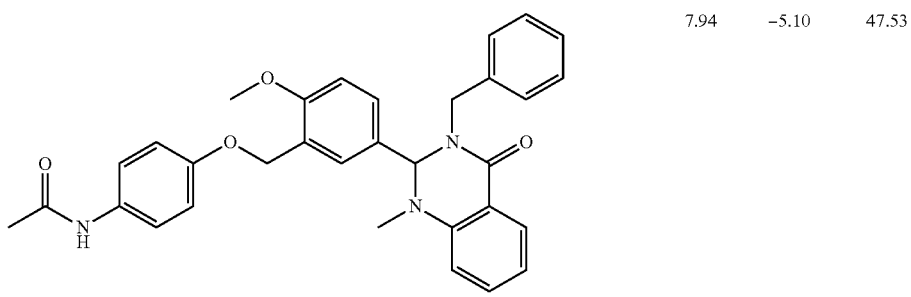 Structure 84 | 7.94 | −5.10 | 47.53 |

-continued
| Structure | AC50 (μM) | Log AC50 | Maximum Activity compared to TSH |
|---|---|---|---|
| 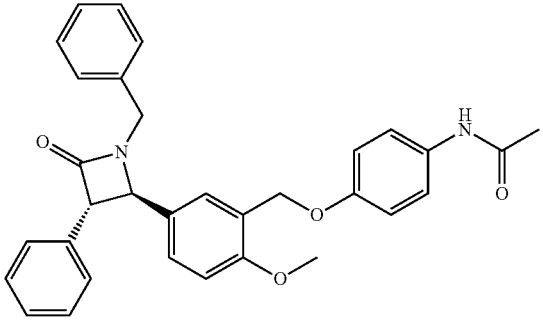<br>Structure 85 | 12.59 | −4.90 | 54.95 |
| 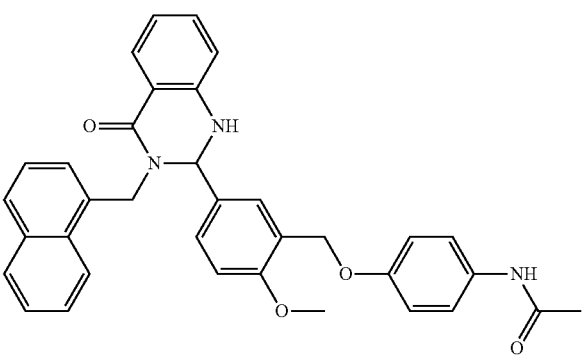<br>Structure 86 | 6.31 | −5.20 | 51.11 |
| 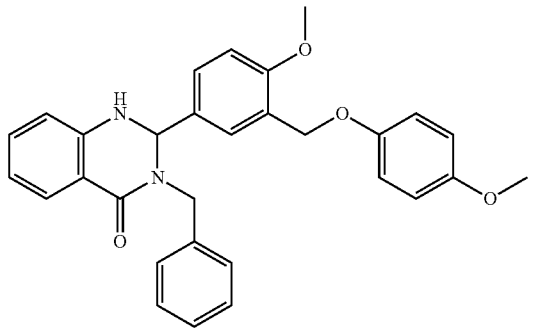<br>Structure 87 | 3.98 | −5.40 | 38.00 |
| 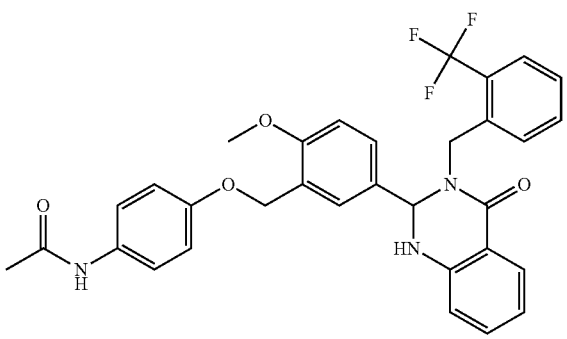<br>Structure 88 | 5.62 | −5.25 | 30.50 |

-continued
| Structure | AC50 (μM) | Log AC50 | Maximum Activity compared to TSH |
|---|---|---|---|
| 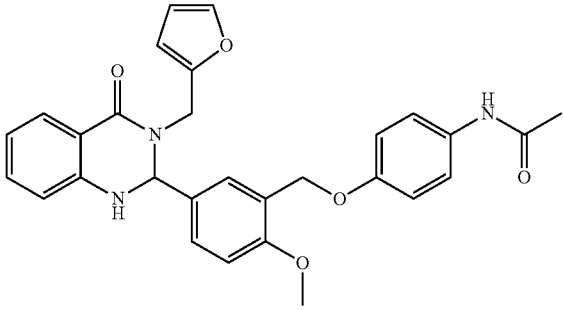<br>Structure 89 | 25.12 | −4.60 | 129.12 |
| 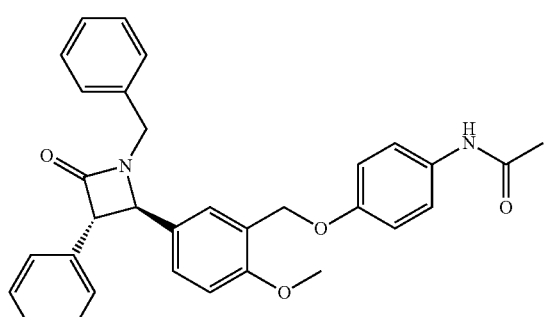<br>Structure 90 | 44.67 | −4.35 | 110.89 |
| 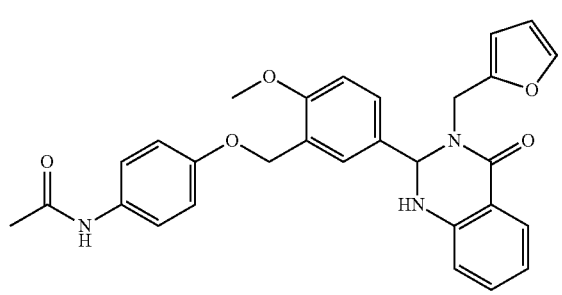<br>Structure 91 | 15.85 | −4.80 | 88.07 |
| 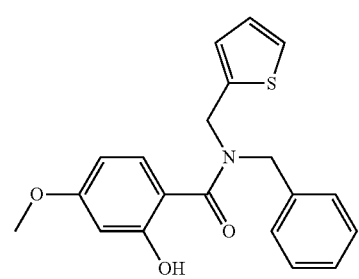<br>Strucutre 92 | 31.62 | −4.50 | 133.48 |

-continued
| Structure | AC50 (μM) | Log AC50 | Maximum Activity compared to TSH |
|---|---|---|---|
| 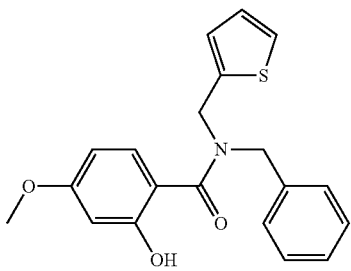 Structure 93 | 28.18 | −4.55 | 111.66 |
| 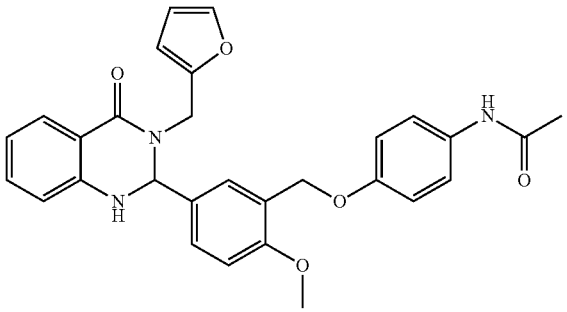 Structure 94 | 25.12 | −4.60 | 160.25 |
| 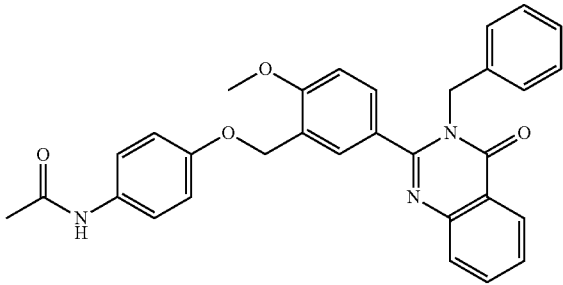 Structure 95 | 12.59 | −4.90 | 138.18 |
| 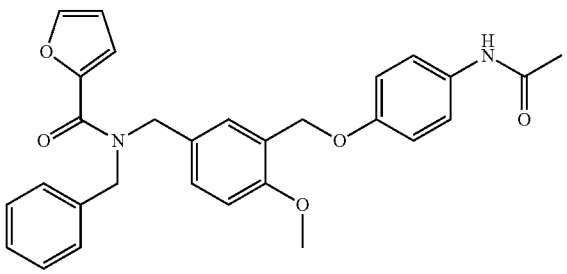 Structure 96 | 14.13 | −4.85 | 124.86 |

-continued
| Structure | AC50 (μM) | Log AC50 | Maximum Activity compared to TSH |
|---|---|---|---|
| 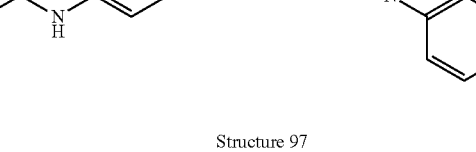<br>Structure 97 | 15.85 | −4.80 | 132.18 |
| 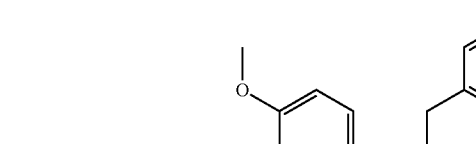<br>Structure 98 | 14.13 | −4.85 | 140.53 |
| 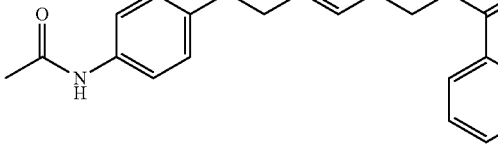<br>Structure 99 | 35.48 | −4.45 | 104.15 |
| 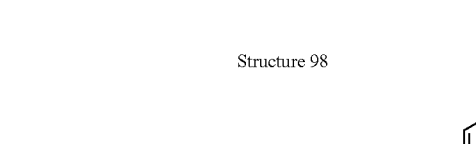<br>Structure 100 | 35.48 | −4.45 | 190.35 |

-continued

| Structure | AC50 (μM) | Log AC50 | Maximum Activity compared to TSH |
|---|---|---|---|
| Structure 101 | 28.18 | −4.55 | 128.51 |
| Structure 102 | 15.85 | −4.80 | 88.66 |
| Structure 103 | 15.85 | −4.80 | 106.72 |
| Structure 104 | 39.81 | −4.40 | 122.31 |

-continued
| Structure | AC50 (μM) | Log AC50 | Maximum Activity compared to TSH |
|---|---|---|---|
| 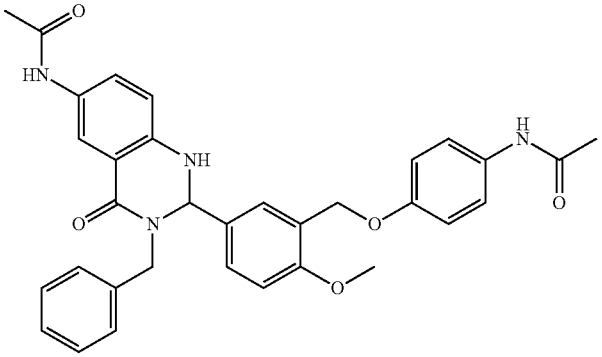<br>Structure 105 | 17.78 | −4.75 | 125.72 |
| 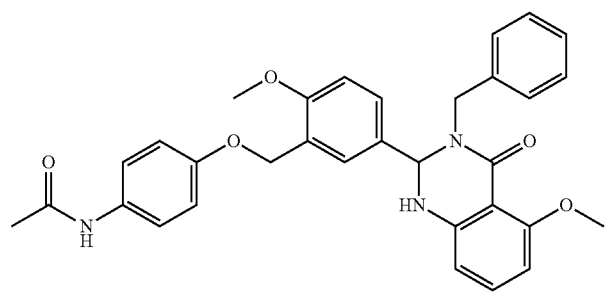<br>Structure 106 | 17.78 | −4.75 | 45.41 |
| 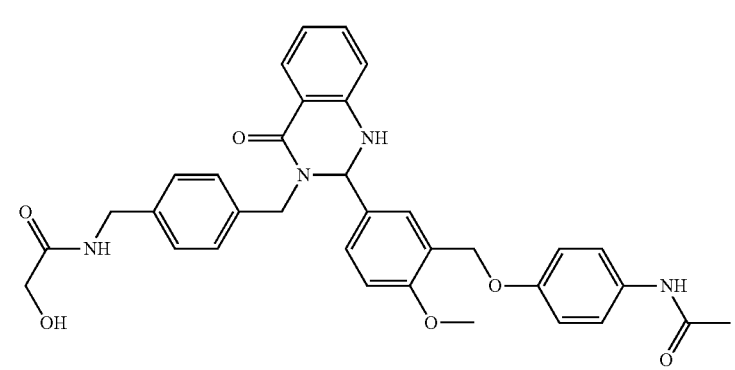<br>Structure 107 | 31.62 | −4.50 | 63.73 |
| 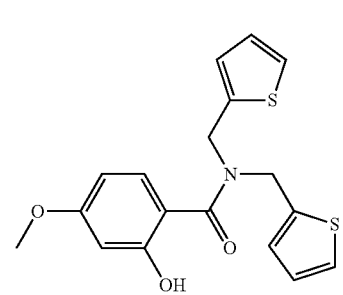<br>Structure 108 | 15.85 | −4.80 | 63.12 |

-continued

| Structure | AC50 (μM) | Log AC50 | Maximum Activity compared to TSH |
|---|---|---|---|
| Structure 109 | 17.78 | −4.75 | 47.53 |
| Structure 110 | 22.39 | −4.65 | 48.00 |
| Structure 111 | 35.48 | −4.45 | 98.46 |
| Structure 112 | 15.85 | −4.80 | 60.92 |

-continued

| Structure | AC50 (μM) | Log AC50 | Maximum Activity compared to TSH |
|---|---|---|---|
| Structure 113 | 39.81 | −4.40 | 63.82 |
| Structure 114 | 25.12 | −4.60 | 51.15 |
| Structure 115 | 39.81 | −4.40 | 66.81 |
| Structure 116 | 35.48 | −4.45 | 54.57 |

| Structure | AC50 (μM) | Log AC50 | Maximum Activity compared to TSH |
|---|---|---|---|
| 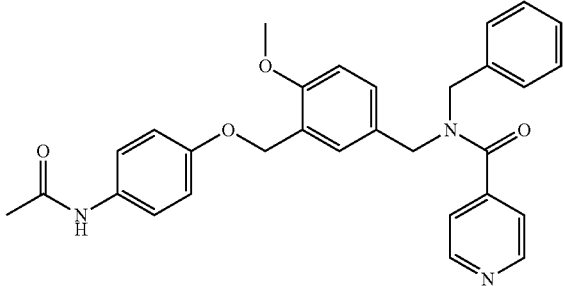<br>Structure 117 | 44.67 | −4.35 | 87.19 |
| 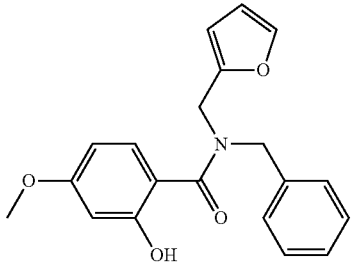<br>Structure 118 | 28.18 | −4.55 | 96.91 |
| 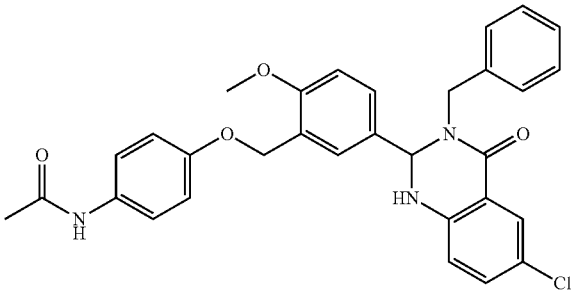<br>Structure 119 | 14.13 | −4.85 | 56.31 |
| 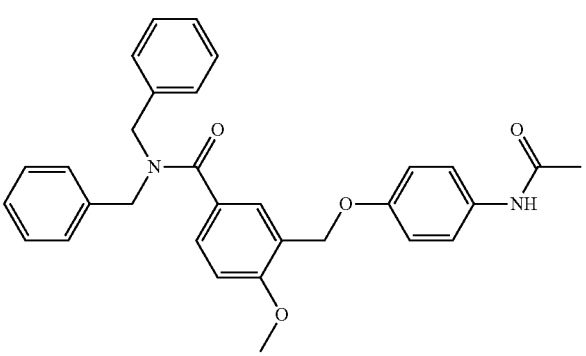<br>Structure 120 | 15.85 | −4.80 | 40.50 |

| Structure | AC50 (μM) | Log AC50 | Maximum Activity compared to TSH |
|---|---|---|---|
| 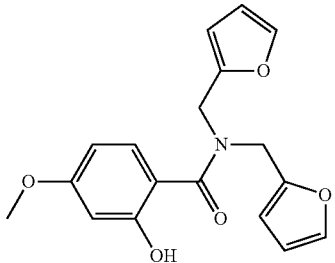 Structure 121 | 39.81 | −4.40 | 38.00 |
| 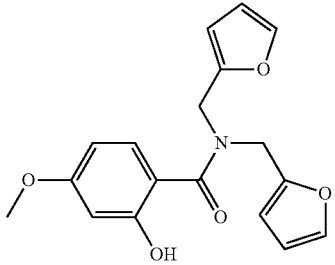 Structure 122 | 50.12 | −4.30 | 61.90 |
| 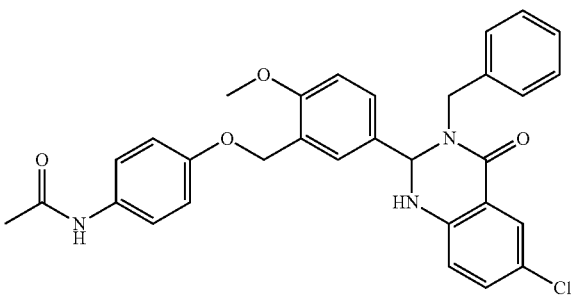 Structure 123 | 14.13 | −4.85 | 83.18 |
| 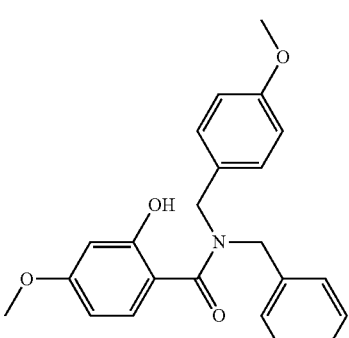 Structure 124 | 31.62 | −4.50 | 62.73 |

-continued

| Structure | AC50 (μM) | Log AC50 | Maximum Activity compared to TSH |
|---|---|---|---|
| Structure 125 | 39.81 | −4.40 | 56.43 |
| Structure 126 | 17.78 | −4.75 | 36.00 |
| Structure 127 | 14.13 | −4.85 | 38.00 |
| Structure 128 | 39.81 | −4.40 | 69.13 |

-continued

| Structure | AC50 (μM) | Log AC50 | Maximum Activity compared to TSH |
|---|---|---|---|
| Structure 129 | 28.18 | −4.55 | 51.77 |
| Structure 130 | 50.12 | −4.30 | 53.70 |
| Structure 131 | 35.48 | −4.45 | 99.01 |
| Structure 132 | 31.62 | −4.50 | 44.00 |

| Structure | AC50 (µM) | Log AC50 | Maximum Activity compared to TSH |
|---|---|---|---|
| 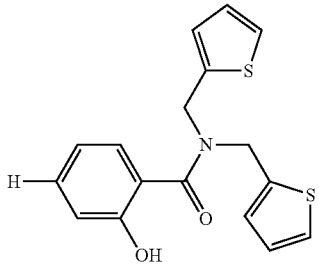 Structure 133 | 31.62 | −4.50 | 55.28 |
| 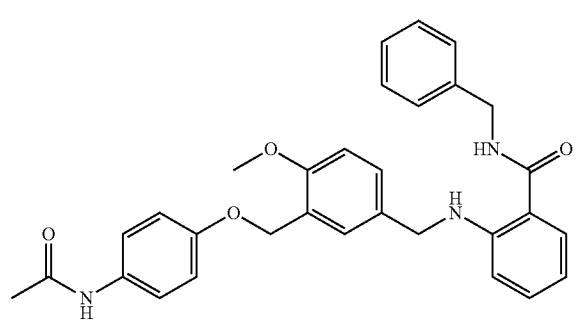 Structure 134 | 8.91 | −5.05 | 30.50 |
| 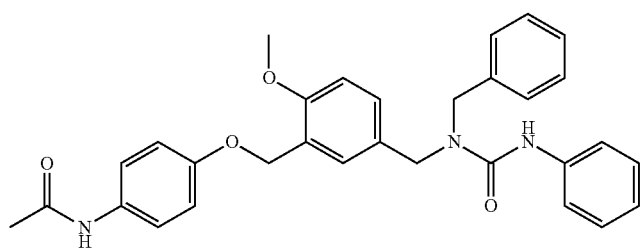 Structure 135 | 44.67 | −4.35 | 48.07 |
| 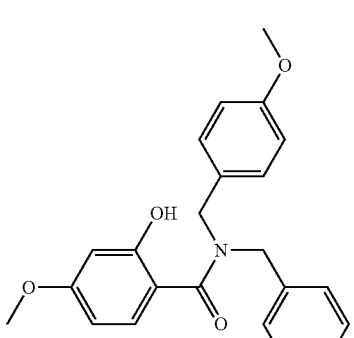 Structure 136 | 28.18 | −4.55 | 37.00 |

-continued
| Structure | AC50 (μM) | Log AC50 | Maximum Activity compared to TSH |
|---|---|---|---|
| 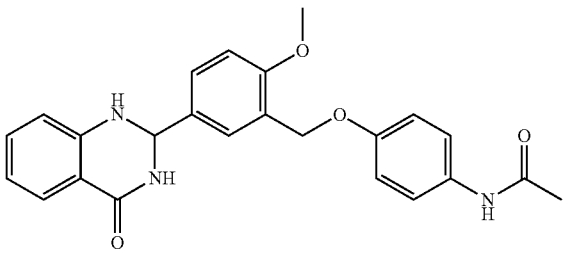<br>Structure 137 | | | inactive |
| 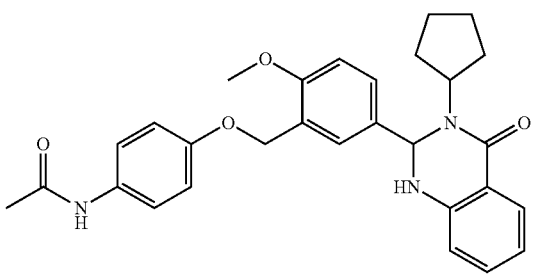<br>Structure 138 | 19.95 | −4.70 | 31.50 |
| 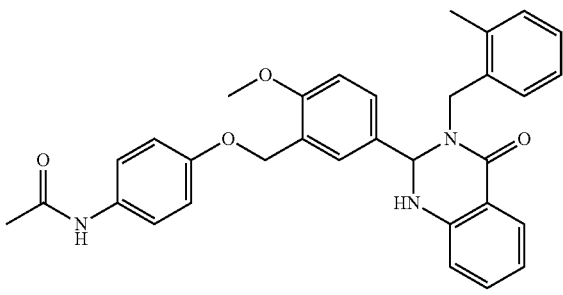<br>Structure 139 | | | inactive |
| 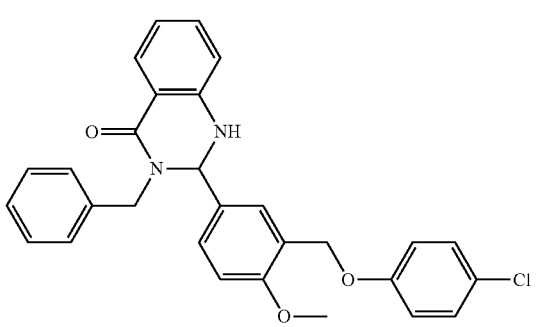<br>Structure 140 | | | inactive |

-continued
| Structure | AC50 (μM) | Log AC50 | Maximum Activity compared to TSH |
|---|---|---|---|
| 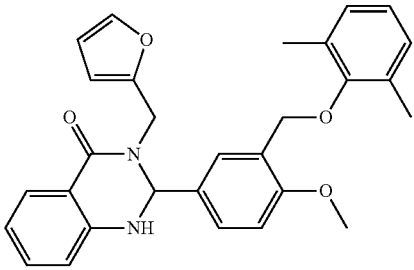<br>Structure 141 | | | inactive |
| 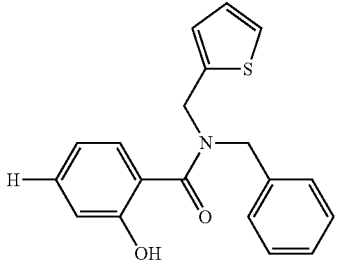<br>Structure 142 | 19.95 | −4.70 | 34.00 |
| 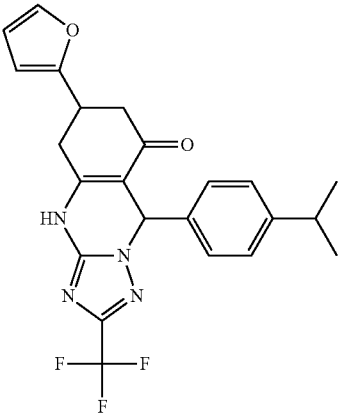<br>Structure 143 | | | inactive |
| 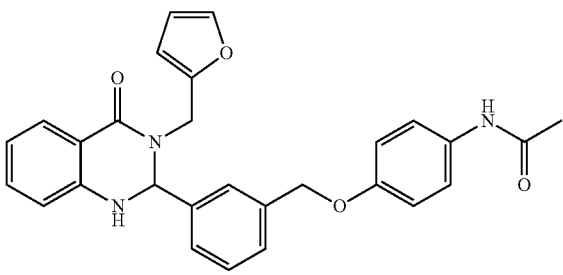<br>Structure 144 | | | inactive |

-continued
| Structure | AC50 (μM) | Log AC50 | Maximum Activity compared to TSH |
|---|---|---|---|
| 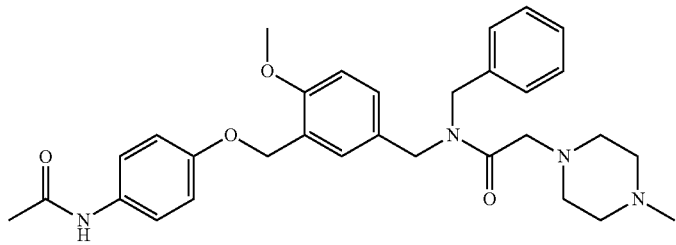 Structure 145 | | | inactive |
| 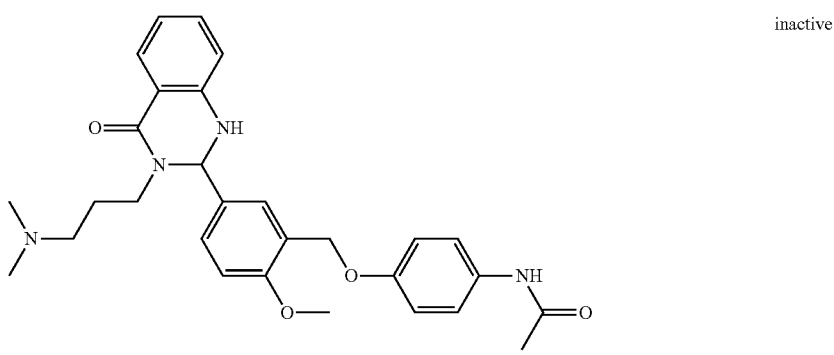 Structure 146 | | | inactive |
| 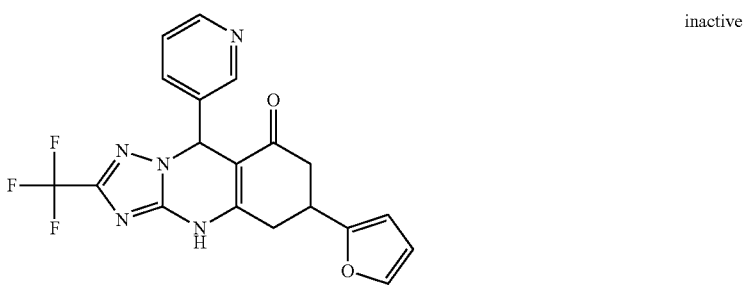 Structure 147 | | | inactive |
| 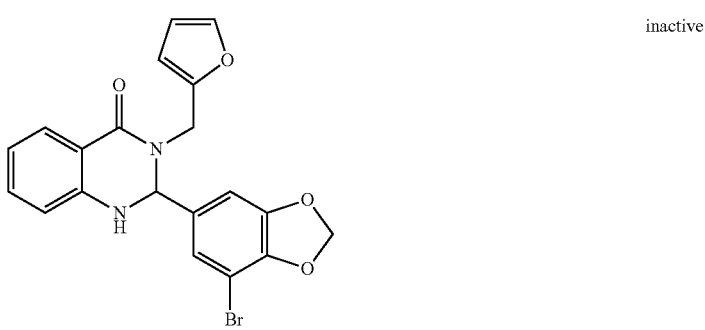 Structure 148 | | | inactive |

-continued
| Structure | AC50 (μM) | Log AC50 | Maximum Activity compared to TSH |
|---|---|---|---|
| 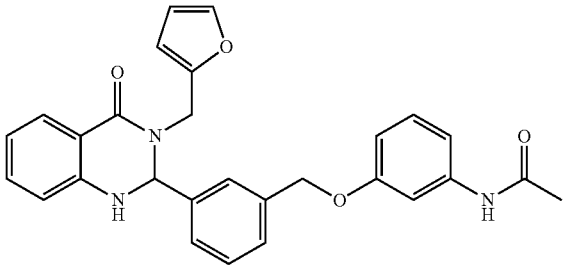
Structure 149 | | | inactive |
| 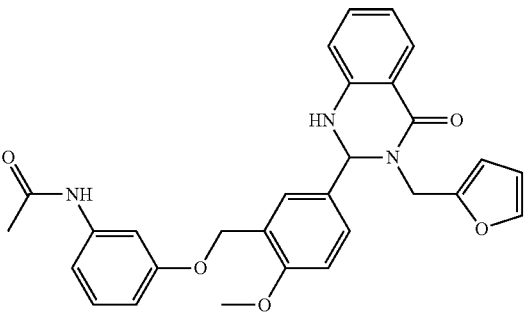
Structure 150 | | | inactive |
| 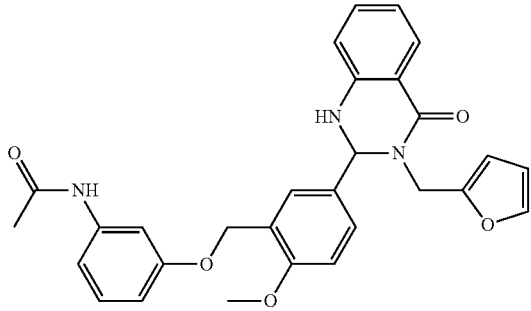
Structure 151 | | | inactive |
| 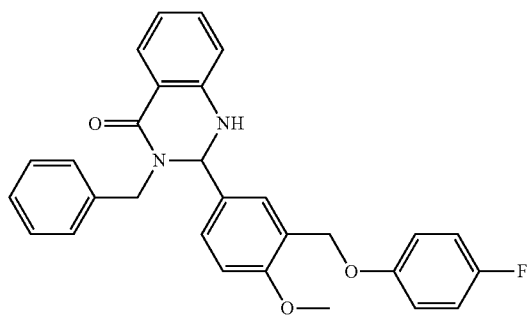
Structure 152 | | | inactive |

-continued

| Structure | AC50 (μM) | Log AC50 | Maximum Activity compared to TSH |
|---|---|---|---|
| Structure 153 | | | inactive |
| Structure 154 | | | inactive |
| Structure 155 | 12.59 | −4.90 | 25.50 |
| Structure 156 | | | inactive |

-continued

| Structure | AC50 (μM) | Log AC50 | Maximum Activity compared to TSH |
|---|---|---|---|
| Structure 157 | | | inactive |
| Structure 158 | | | inactive |
| Structure 159 | | | inactive |
| Structure 160 | 50.12 | −4.30 | 28.00 |

-continued

| Structure | AC50 (μM) | Log AC50 | Maximum Activity compared to TSH |
|---|---|---|---|
| Structure 161 | | | inactive |
| Structure 162 | | | inactive |
| Structure 163 | | | inactive |
| Structure 164 | | | inactive |

-continued
| Structure | AC50 (μM) | Log AC50 | Maximum Activity compared to TSH |
|---|---|---|---|
| 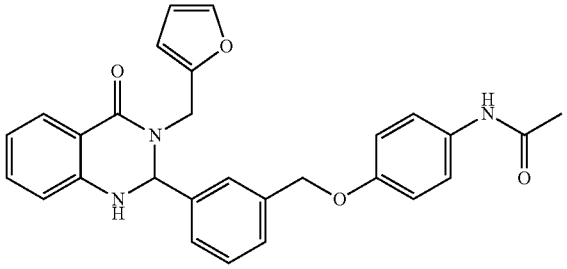<br>Structure 165 | | | inactive |
| 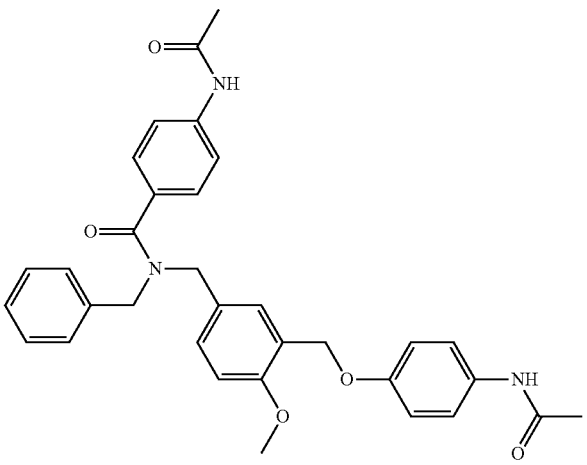<br>Structure 166 | | | inactive |
| 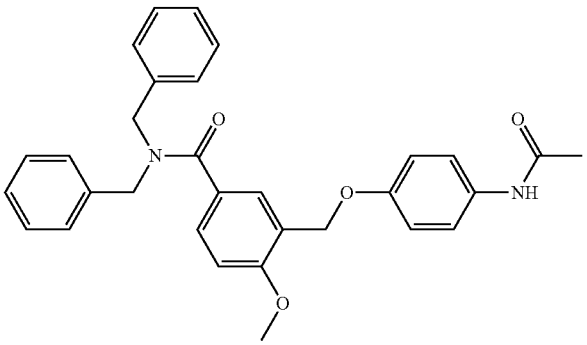<br>Structure 167 | 14.13 | −4.85 | 24.50 |

-continued

| Structure | AC50 (μM) | Log AC50 | Maximum Activity compared to TSH |
|---|---|---|---|
| Structure 168 | | | inactive |
| Structure 169 | 50.12 | −4.30 | 34.00 |
| Structure 170 | | | inactive |
| Structure 171 | | | inactive |

-continued

| Structure | AC50 (μM) | Log AC50 | Maximum Activity compared to TSH |
|---|---|---|---|
| Structure 172 | | | inactive |
| Structure 173 | 15.85 | −4.80 | 30.00 |
| Structure 174 | | | inactive |

-continued
| Structure | AC50 (μM) | Log AC50 | Maximum Activity compared to TSH |
|---|---|---|---|
| 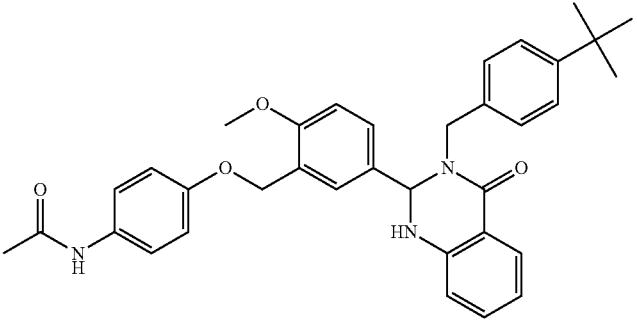  Structure 175 | | | inactive |
| 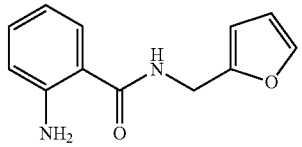  Structure 176 | | | inactive |
| 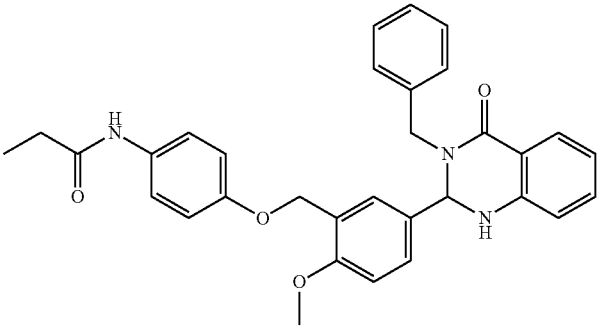  Structure 177 | 5.62 | −5.25 | 29.00 |
| 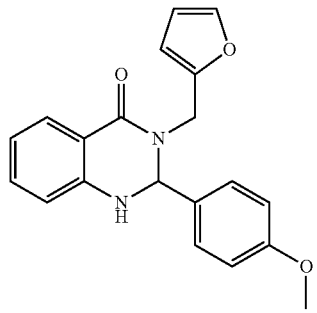  Structure 178 | | | inactive |

-continued
| Structure | AC50 (μM) | Log AC50 | Maximum Activity compared to TSH |
|---|---|---|---|
| 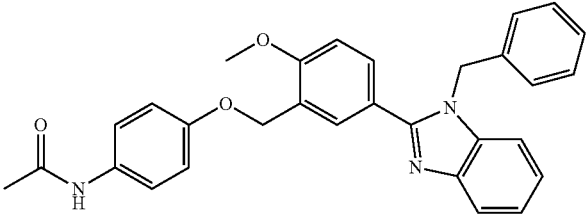
Structure 179 | | | inactive |
| 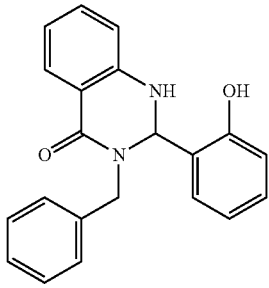
Structure 180 | | | inactive |
| 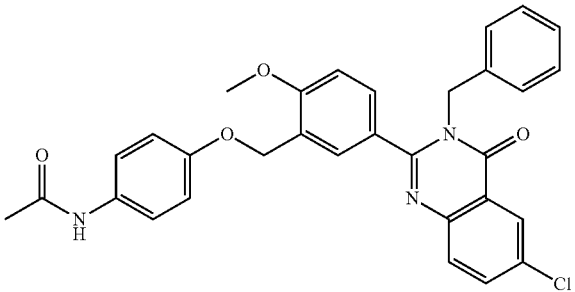
Structure 181 | 3.98 | −5.40 | 22.50 |
| 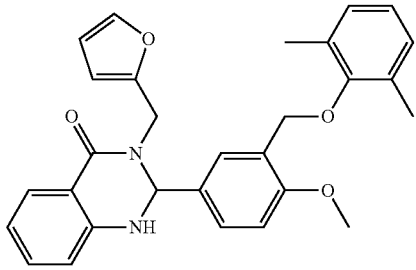
Structure 182 | | | inactive |

-continued
| Structure | AC50 (μM) | Log AC50 | Maximum Activity compared to TSH |
|---|---|---|---|
| 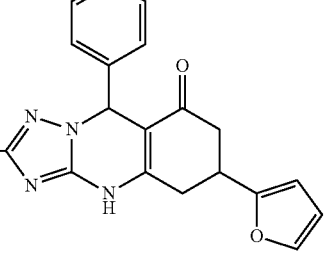  Structure 183 | | | inactive |
| 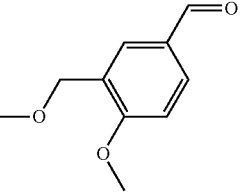  Structure 184 | | | inactive |
| 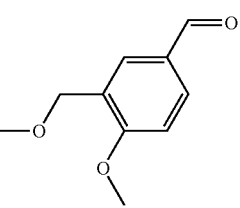  Structure 185 | | | inactive |
|   Structure 186 | | | inactive |

-continued
| Structure | AC50 (μM) | Log AC50 | Maximum Activity compared to TSH |
|---|---|---|---|
| 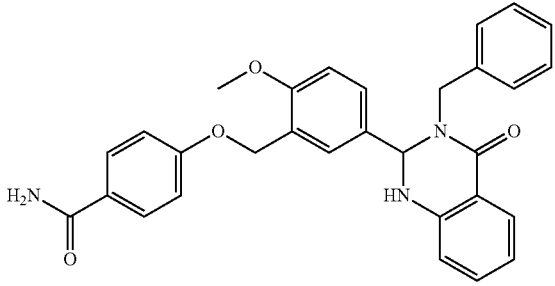  Structure 187 | | | inactive |
| 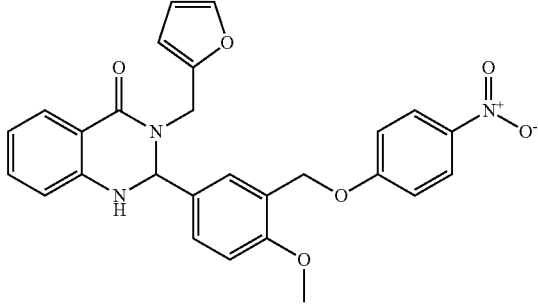  Structure 188 | | | inactive |
| 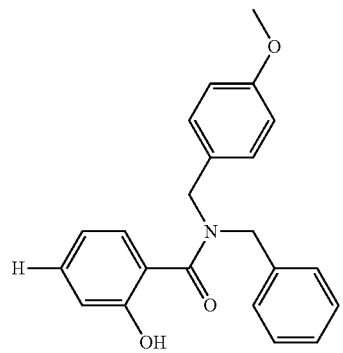  Structure 189 | 22.39 | −4.65 | 24.00 |
| 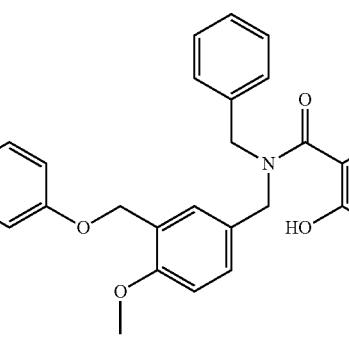  Structure 190 | | | inactive |

| Structure | AC50 (μM) | Log AC50 | Maximum Activity compared to TSH |
|---|---|---|---|
| 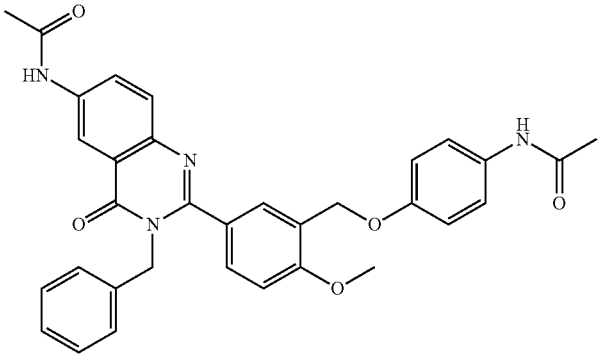<br>Structure 191 | | | inactive |
| 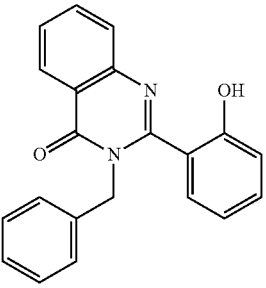<br>Structure 192 | | | inactive |
| 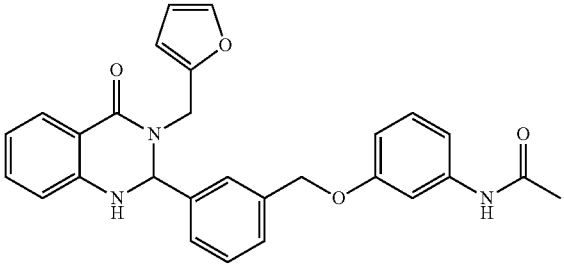<br>Structure 193 | | | inactive |
| 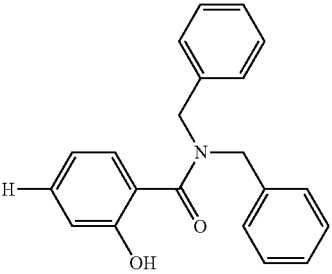<br>Structure 194 | 31.62 | −4.50 | 27.50 |

-continued
| Structure | AC50 (μM) | Log AC50 | Maximum Activity compared to TSH |
|---|---|---|---|
| 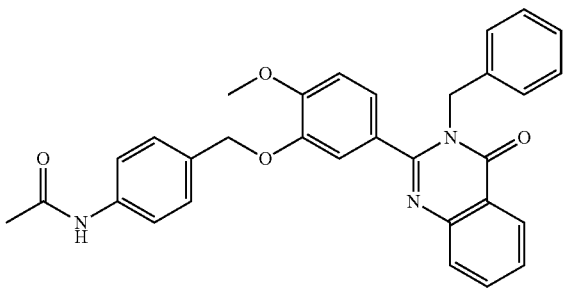<br>Structure 195 | | | inactive |
| 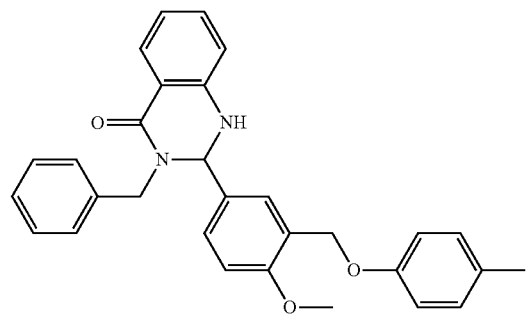<br>Structure 196 | | | inactive |
| 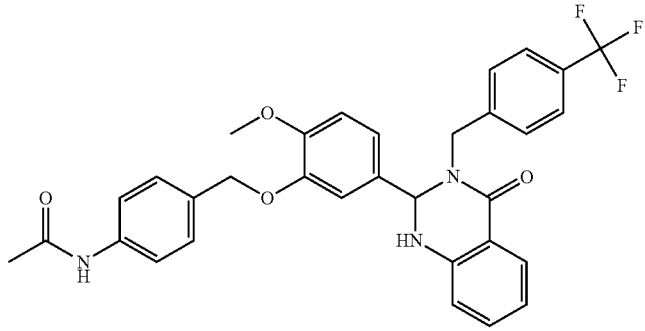<br>Structure 197 | 2.82 | −5.55 | 17.00 |
| 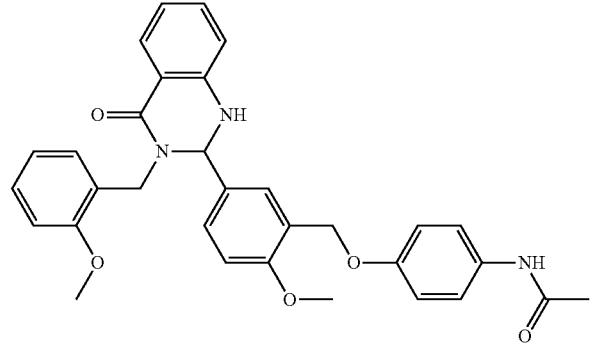<br>Structure 198 | 19.95 | −4.70 | 18.00 |

-continued

| Structure | AC50 (μM) | Log AC50 | Maximum Activity compared to TSH |
|---|---|---|---|
| Structure 199 | | | inactive |
| Structure 200 | 28.18 | −4.55 | 38.00 |
| Structure 201 | | | inactive |
| Structure 202 | | | inactive |

-continued

| Structure | AC50 (μM) | Log AC50 | Maximum Activity compared to TSH |
|---|---|---|---|
| Structure 203 | | | inactive |
| Structure 204 | | | inactive |
| Structure 205 | | | inactive |
| Structure 206 | | | inactive |

-continued
| Structure | AC50 (μM) | Log AC50 | Maximum Activity compared to TSH |
|---|---|---|---|
| 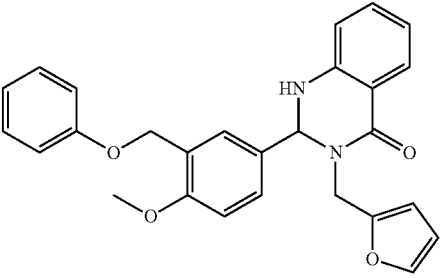
Structure 207 | | | inactive |
| 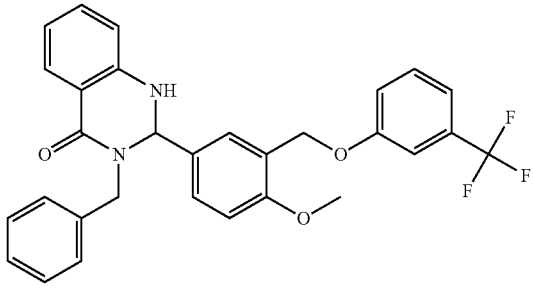
Structure 208 | | | inactive |
| 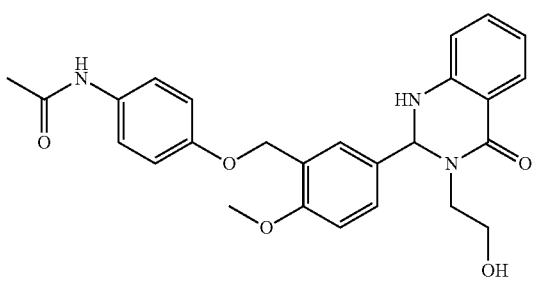
Structure 209 | | | inactive |
| 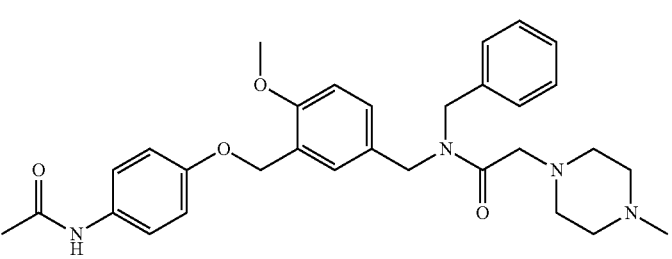
Structure 210 | | | inactive |

-continued
| Structure | AC50 (μM) | Log AC50 | Maximum Activity compared to TSH |
|---|---|---|---|
| 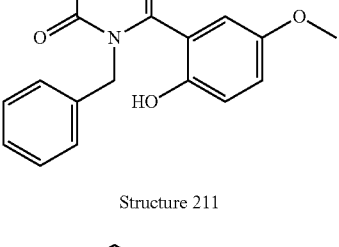 Structure 211 | | | inactive |
| 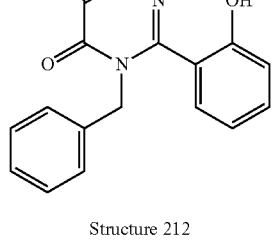 Structure 212 | | | inactive |
| 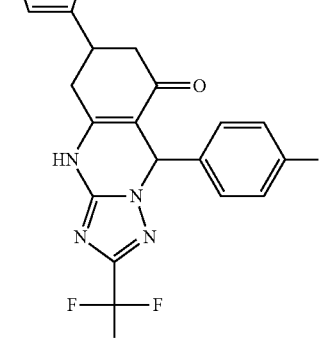 Structure 213 | | | inactive |
| 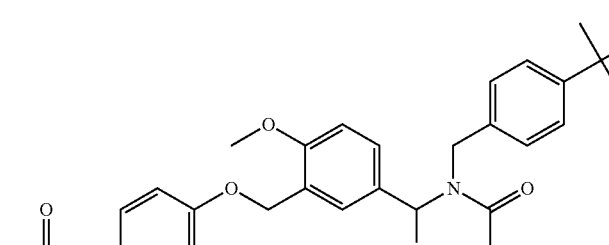 Structure 214 | | | inactive |

-continued
| Structure | AC50 (μM) | Log AC50 | Maximum Activity compared to TSH |
|---|---|---|---|
| 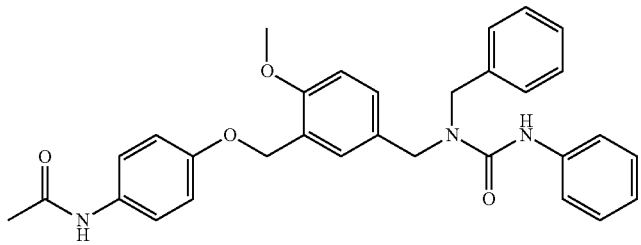<br>Structure 215 | 5.62 | −5.25 | 20.00 |
| 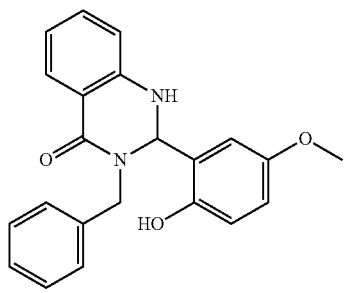<br>Structure 216 | inactive | | |
| 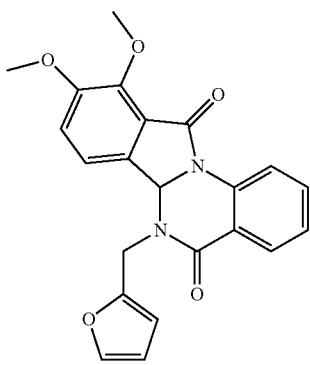<br>Structure 217 | inactive | | |
| 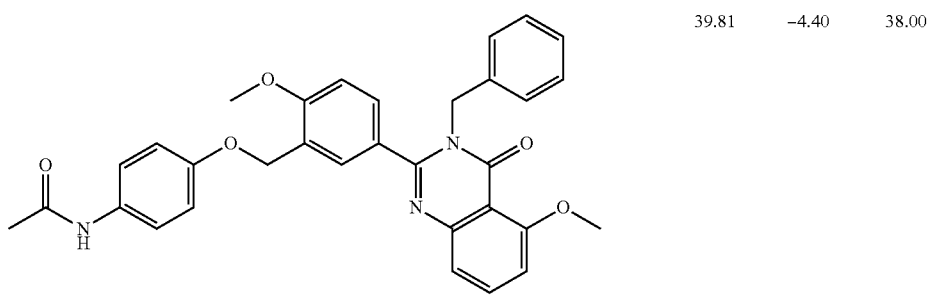<br>Structure 218 | 39.81 | −4.40 | 38.00 |

-continued

| Structure | AC50 (μM) | Log AC50 | Maximum Activity compared to TSH |
|---|---|---|---|
| Structure 219 | | | inactive |
| Structure 220 | 17.78 | −4.75 | 32.00 |
| Structure 221 | | | inactive |
| Structure 222 | | | inactive |

-continued

| Structure | AC50 (μM) | Log AC50 | Maximum Activity compared to TSH |
|---|---|---|---|
| Structure 223 | | | inactive |
| Structure 224 | | | inactive |
| Structure 225 | | | inactive |
| Structure 226 | | | inactive |

| Structure | AC50 (μM) | Log AC50 | Maximum Activity compared to TSH |
|---|---|---|---|
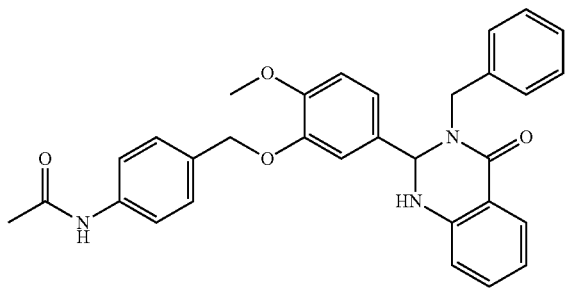
Structure 227
inactive
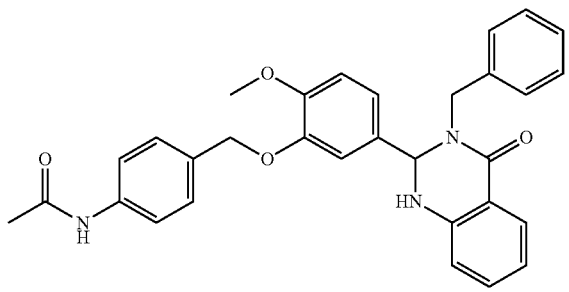
Structure 228
inactive
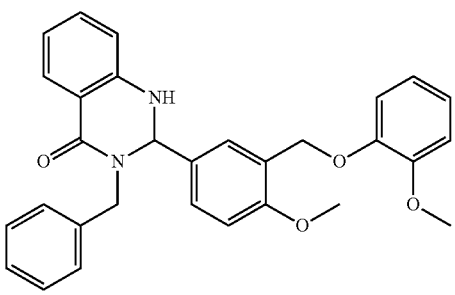
Structure 229
8.91  −5.05  23.50
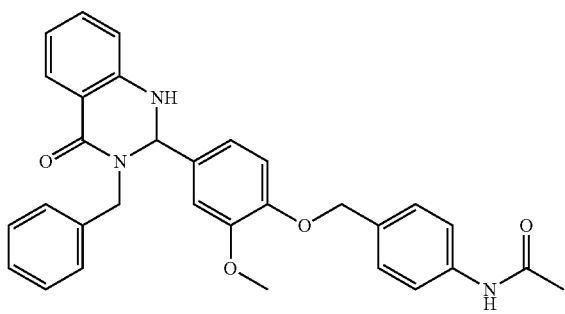
Structure 230
inactive -continued
| Structure | AC50 (μM) | Log AC50 | Maximum Activity compared to TSH |
|---|---|---|---|
| Structure 231 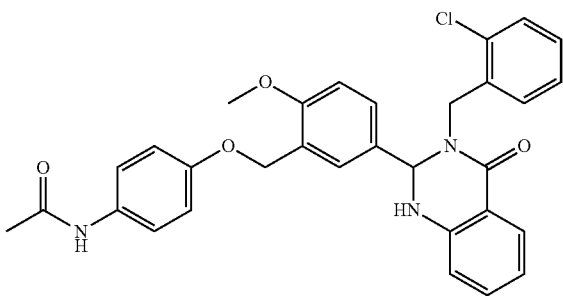 | 3.55 | −5.45 | 16.00 |
| Structure 232 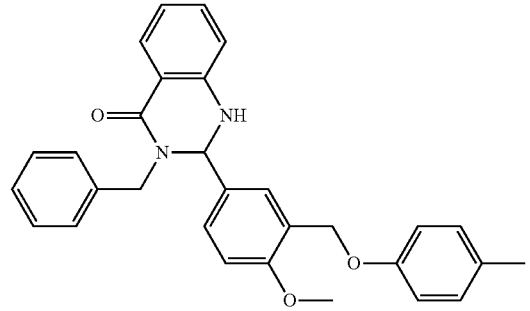 | | | inactive |
| Structure 233 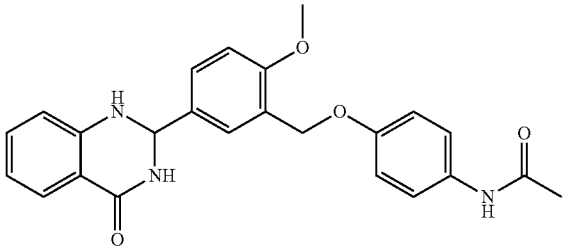 | | | inactive |
| Structure 234 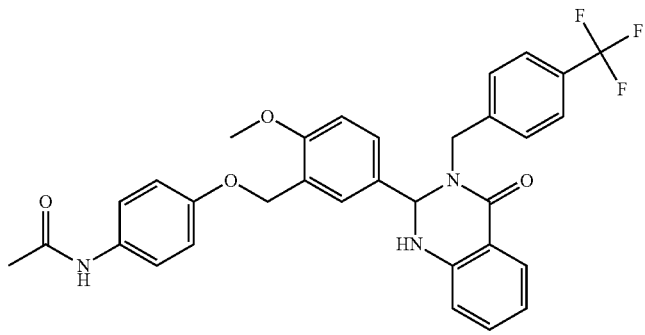 | 8.91 | −5.05 | 18.00 |

-continued
| Structure | AC50 (μM) | Log AC50 | Maximum Activity compared to TSH |
|---|---|---|---|
| 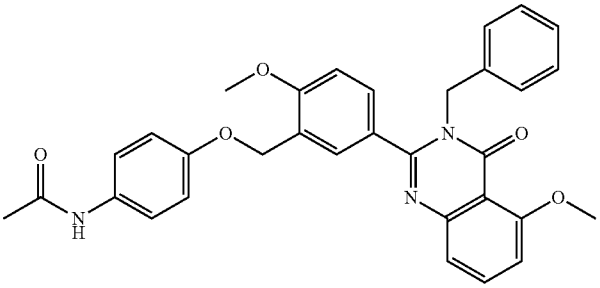  Structure 235 | | | inactive |
| 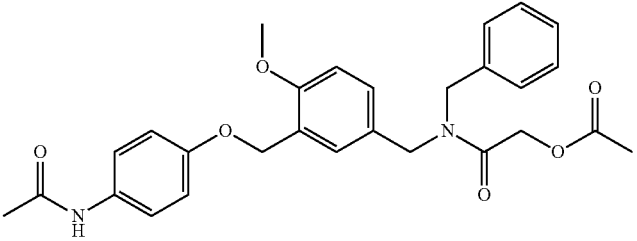  Structure 236 | 35.48 | −4.45 | 32.00 |
| 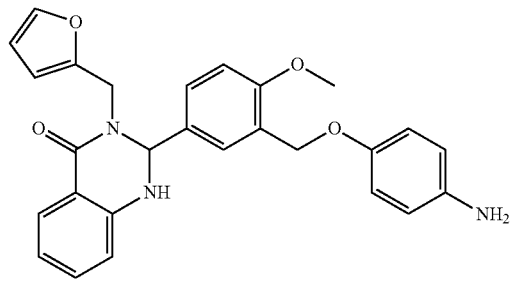  Structure 237 | | | inactive |
| 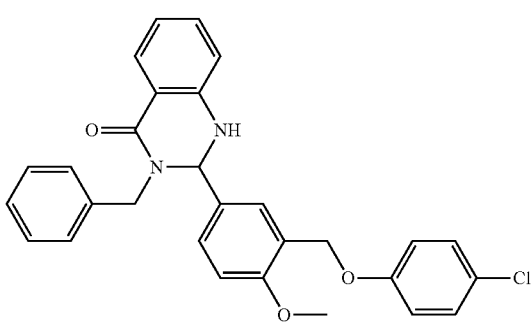  Structure 238 | | | inactive |

-continued
| Structure | AC50 (μM) | Log AC50 | Maximum Activity compared to TSH |
|---|---|---|---|
| 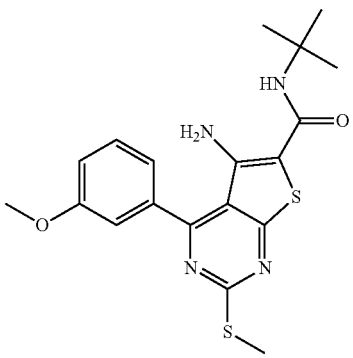<br>Structure 239 | 17.78 | −4.75 | 30.00 |
| 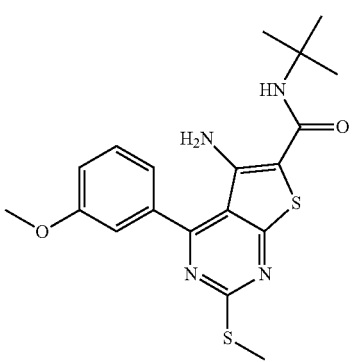<br>Structure 240 | | | inactive |
| 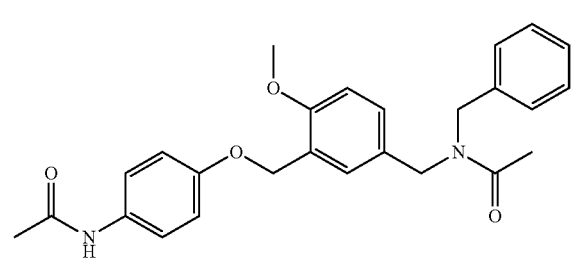<br>Structure 241 | | | inactive |
| 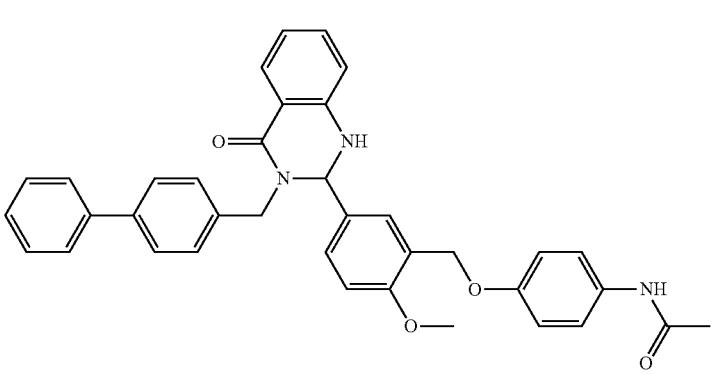<br>Structure 242 | | | inactive |

| Structure | AC50 (μM) | Log AC50 | Maximum Activity compared to TSH |
|---|---|---|---|
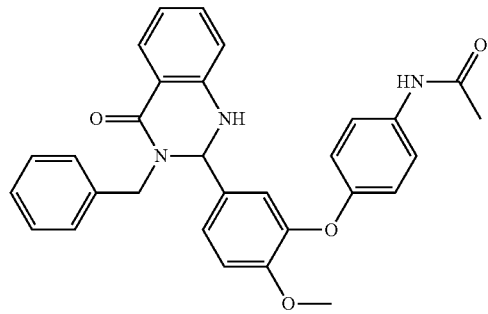
Structure 243
inactive
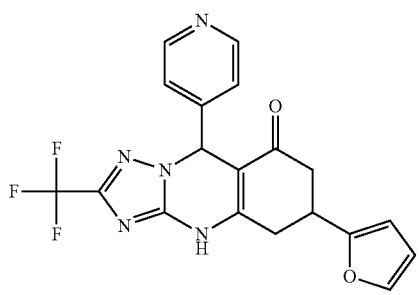
Structure 244
inactive
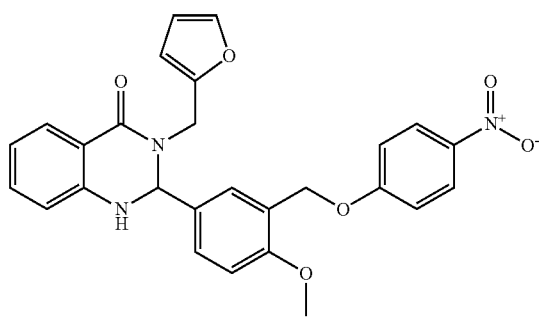
Structure 245
inactive
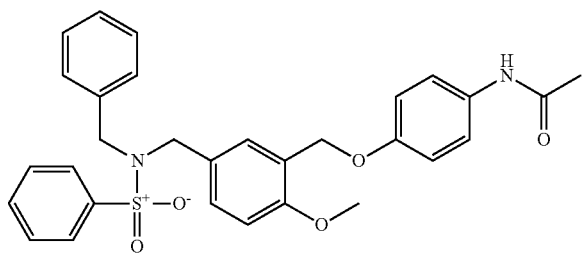
Structure 246
inactive -continued

| Structure | AC50 (μM) | Log AC50 | Maximum Activity compared to TSH |
|---|---|---|---|
| Structure 247 | | | inactive |
| Structure 248 | 70.79 | −4.15 | 32.00 |
| Structure 249 | 50.12 | −4.30 | 38.00 |
| Structure 250 | | | inactive |

-continued
| Structure | AC50 (μM) | Log AC50 | Maximum Activity compared to TSH |
|---|---|---|---|
| 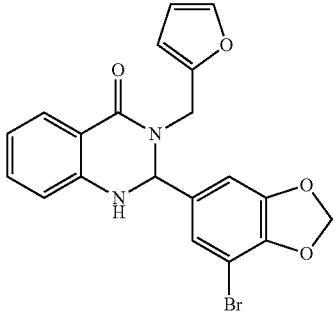
Structure 251 | | | inactive |
| 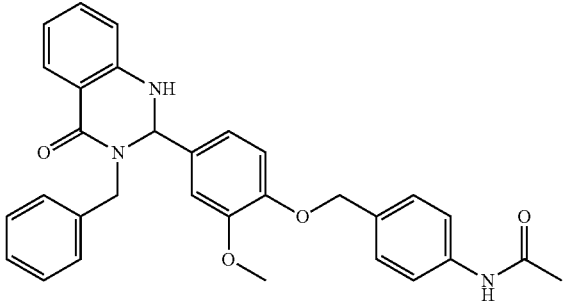
Structure 252 | | | inactive |
| 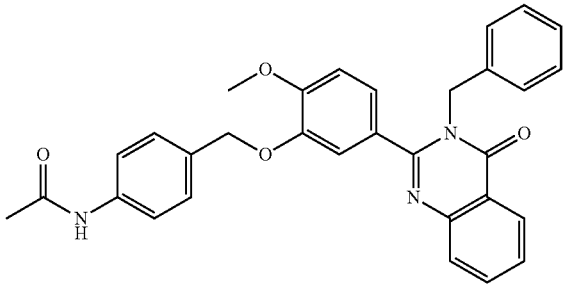
Structure 253 | | | inactive |
| 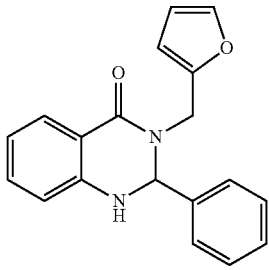
Structure 254 | | | inactive |

| Structure | AC50 (μM) | Log AC50 | Maximum Activity compared to TSH |
|---|---|---|---|
| Structure 255 | | | inactive |
| Structure 256 | 5.01 | −5.30 | 24.00 |
| Structure 257 | 19.95 | −4.70 | 20.00 |
| Structure 258 | 28.18 | −4.55 | 21.50 |

| Structure | AC50 (μM) | Log AC50 | Maximum Activity compared to TSH |
|---|---|---|---|
| 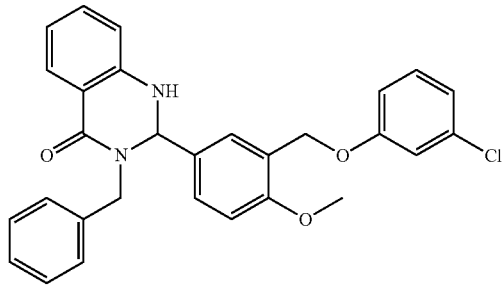<br>Structure 259 | | | inactive |
| 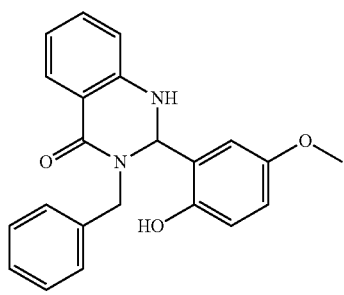<br>Structure 260 | | | inactive |
| 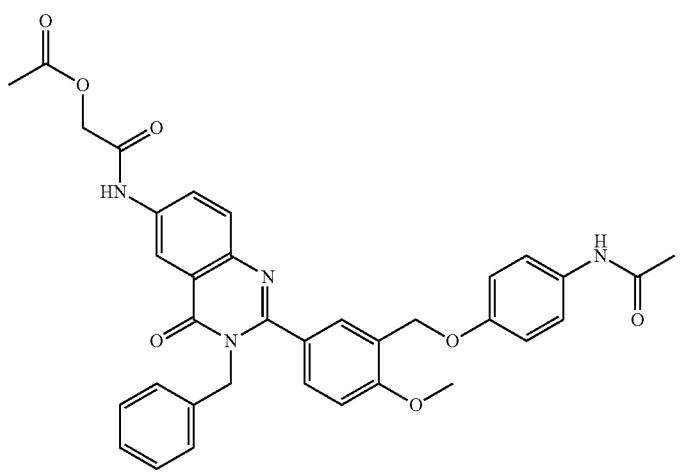<br>Structure 261 | | | inactive |

-continued
| Structure | AC50 (μM) | Log AC50 | Maximum Activity compared to TSH |
|---|---|---|---|
| 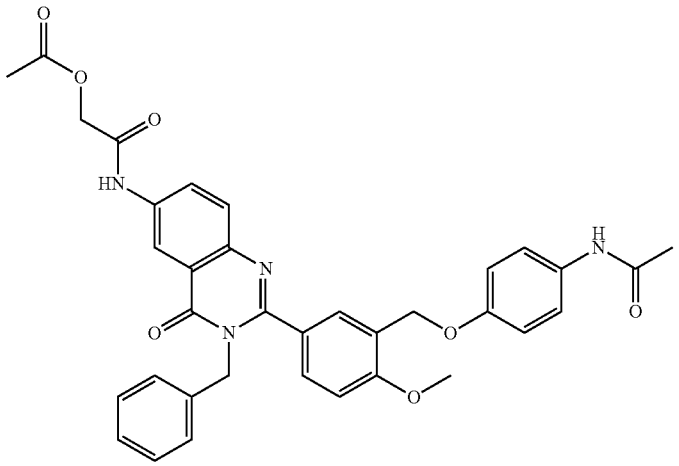
Structure 262 | | | inactive |
| 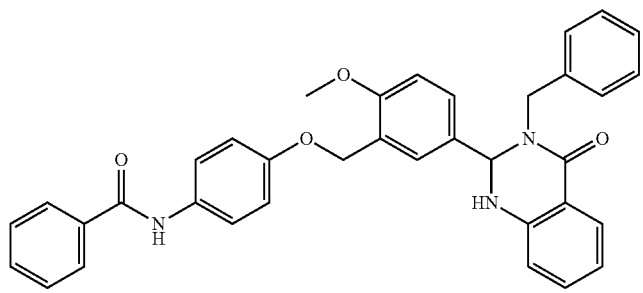
Structure 263 | | | inactive |
| 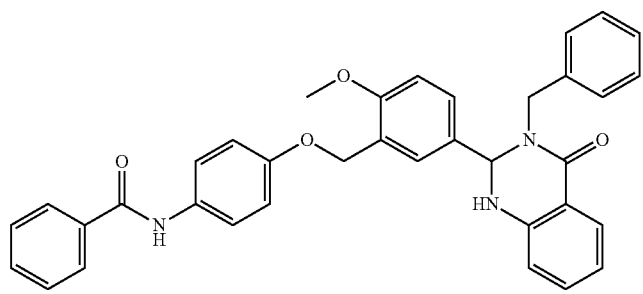
Structure 264 | | | inactive |

-continued

| Structure | AC50 (μM) | Log AC50 | Maximum Activity compared to TSH |
|---|---|---|---|
| Structure 265 | 6.31 | −5.20 | 24.00 |
| Structure 266 | | inactive | |
| Structure 267 | 7.94 | −5.10 | 24.50 |
| Structure 268 | | inactive | |

-continued
| Structure | AC50 (μM) | Log AC50 | Maximum Activity compared to TSH |
|---|---|---|---|
| 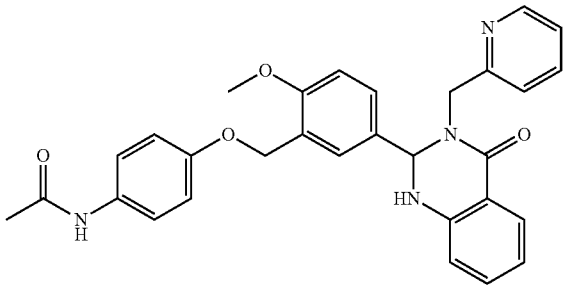
Structure 269 | 25.12 | −4.60 | 28.00 |
| 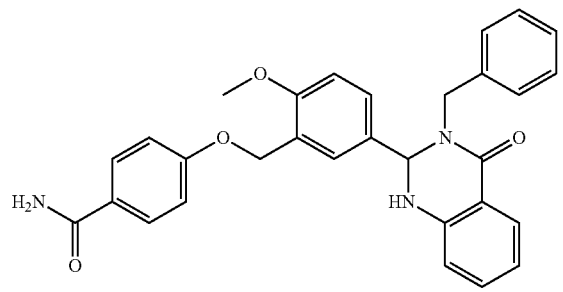
Structure 270 | | | inactive |
| 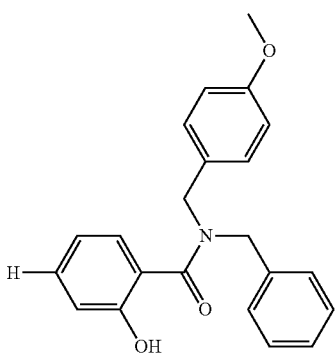
Structure 271 | | | inactive |
| 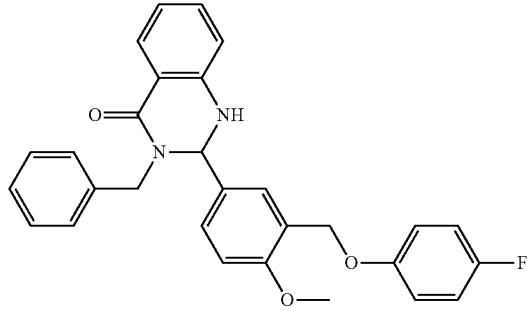
Structure 272 | | | inactive |

-continued
| Structure | AC50 (μM) | Log AC50 | Maximum Activity compared to TSH |
|---|---|---|---|
| 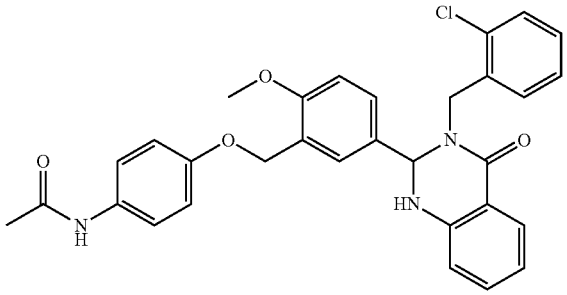<br>Structure 273 | 2.51 | −5.60 | 11.00 |
| 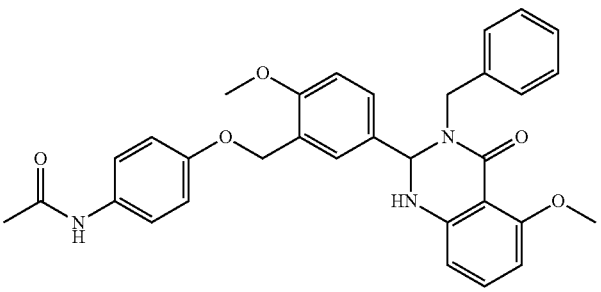<br>Structure 274 | 19.95 | −4.70 | 28.00 |
| 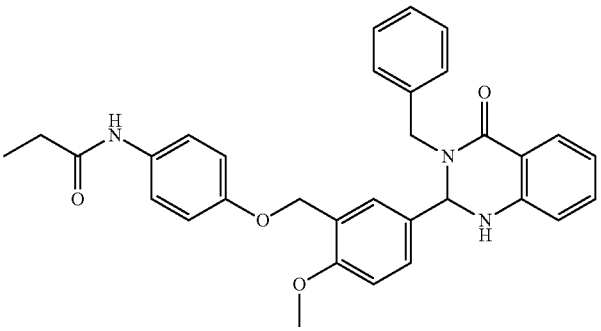<br>Structure 275 | 7.94 | −5.10 | 23.50 |
| 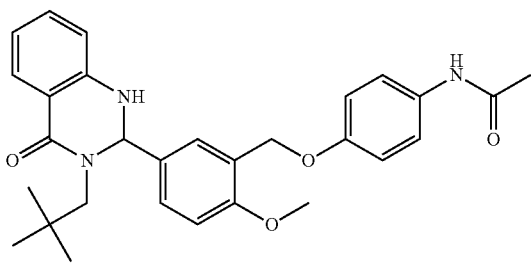<br>Structure 276 | 25.12 | −4.60 | 32.00 |

-continued
| Structure | AC50 (μM) | Log AC50 | Maximum Activity compared to TSH |
|---|---|---|---|
| 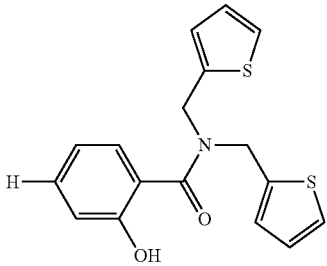<br>Structure 277 | | | inactive |
| 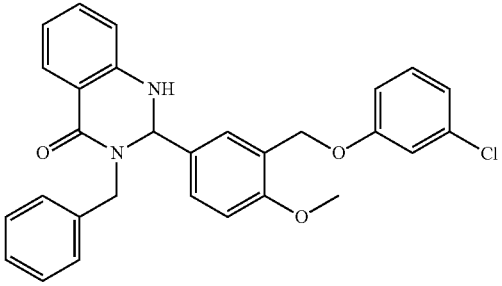<br>Structure 278 | | | inactive |
| 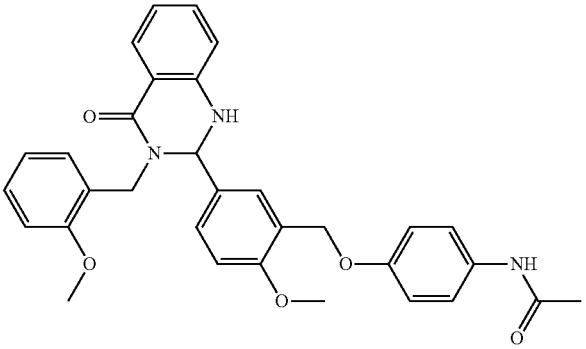<br>Structure 279 | 4.47 | −5.35 | 20.50 |
| 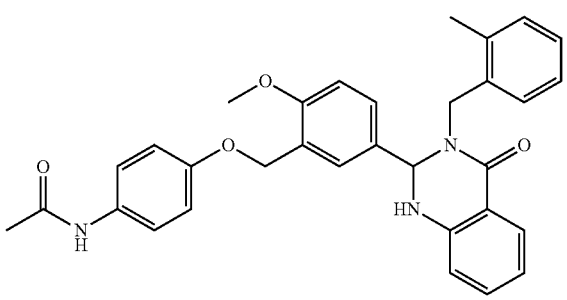<br>Structure 280 | 17.78 | −4.75 | 24.00 |

-continued

| Structure | AC50 (μM) | Log AC50 | Maximum Activity compared to TSH |
|---|---|---|---|
| Structure 281 | 5.62 | −5.25 | 22.00 |
| Structure 282 | | | inactive |
| Structure 283 | | | inactive |
| Structure 284 | | | inactive |

-continued

| Structure | AC50 (μM) | Log AC50 | Maximum Activity compared to TSH |
|---|---|---|---|
| Structure 285 | | | inactive |
| Structure 286 | | | inactive |
| Structure 287 | 22.39 | −4.65 | 30.00 |
| Structure 288 | 2.24 | −5.65 | 20.50 |

-continued
| Structure | AC50 (μM) | Log AC50 | Maximum Activity compared to TSH |
|---|---|---|---|
| 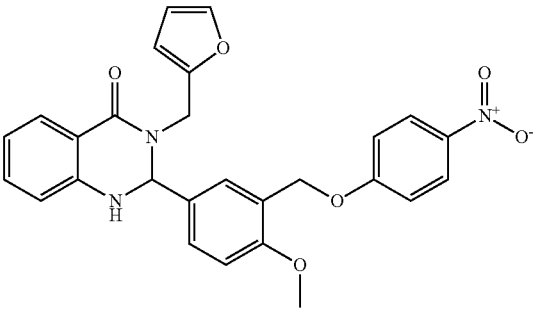\nStructure 289 | | | inactive |
| 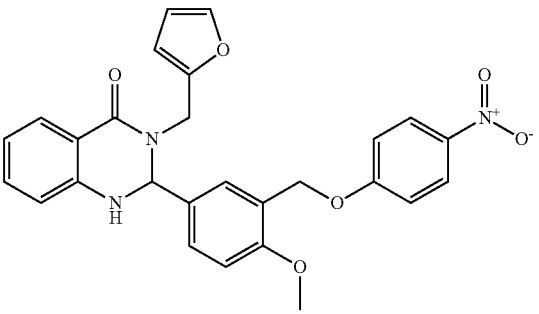\nStructure 290 | | | inactive |
| 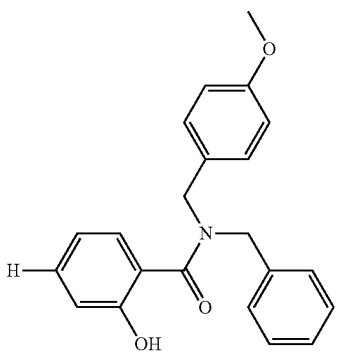\nStructure 291 | 35.48 | −4.45 | 38.00 |

| Structure | AC50 (μM) | Log AC50 | Maximum Activity compared to TSH |
|---|---|---|---|
| 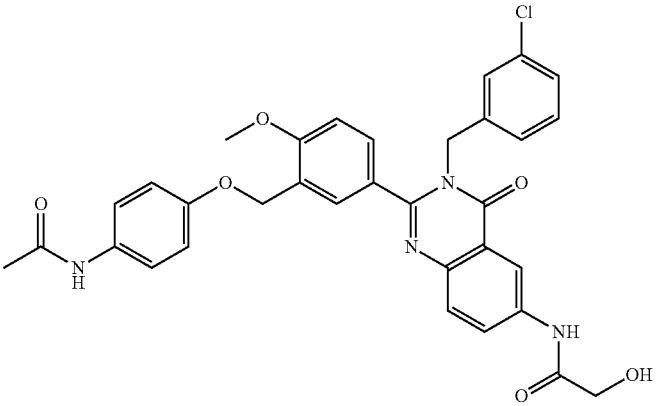<br>Structure 292 | | | inactive |
| 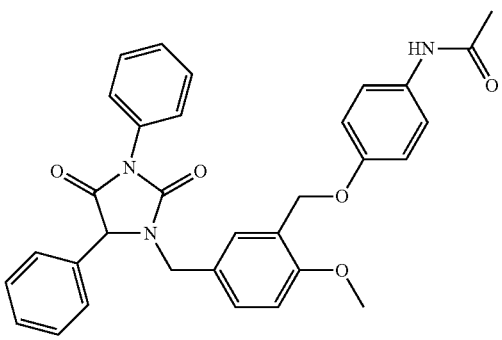<br>Structure 293 | | | inactive |
| 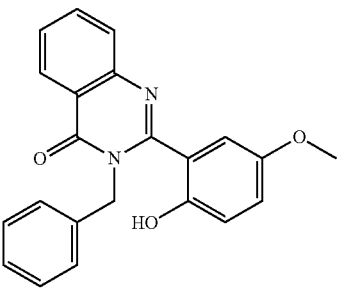<br>Structure 294 | | | inactive |

The EC$_{50}$ Values Determined Via the Confirmatory cAMP Assay for Several Compounds were:

| Compound 3 | 590 nM |
|---|---|
| Compound 3/4 | 25 nM |
| Compound 3/5 | 38 nM |
| Compound 3/1 | 100 nM |
| Compound 3/2 | 541 nM |

FIG. 1 shows that the compounds disclosed herein are TSHR-selective agonists since they exhibit no agonist activity against LHCGR or FSHR.

Figure 2:
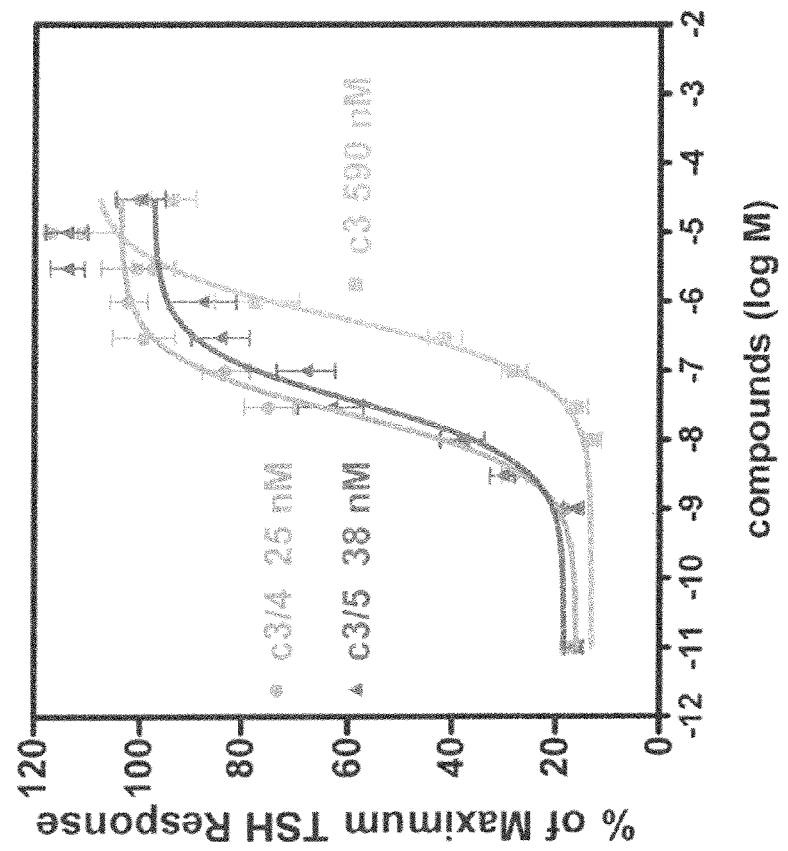
FIG. 2 is a graph depicting data demonstrating the potency of several compounds disclosed herein.

FIG. 2 is a graph depicting data in HEK EM 293 cells stably expressing the TSHR demonstrating the potency of several compounds disclosed herein.

Figure 3:
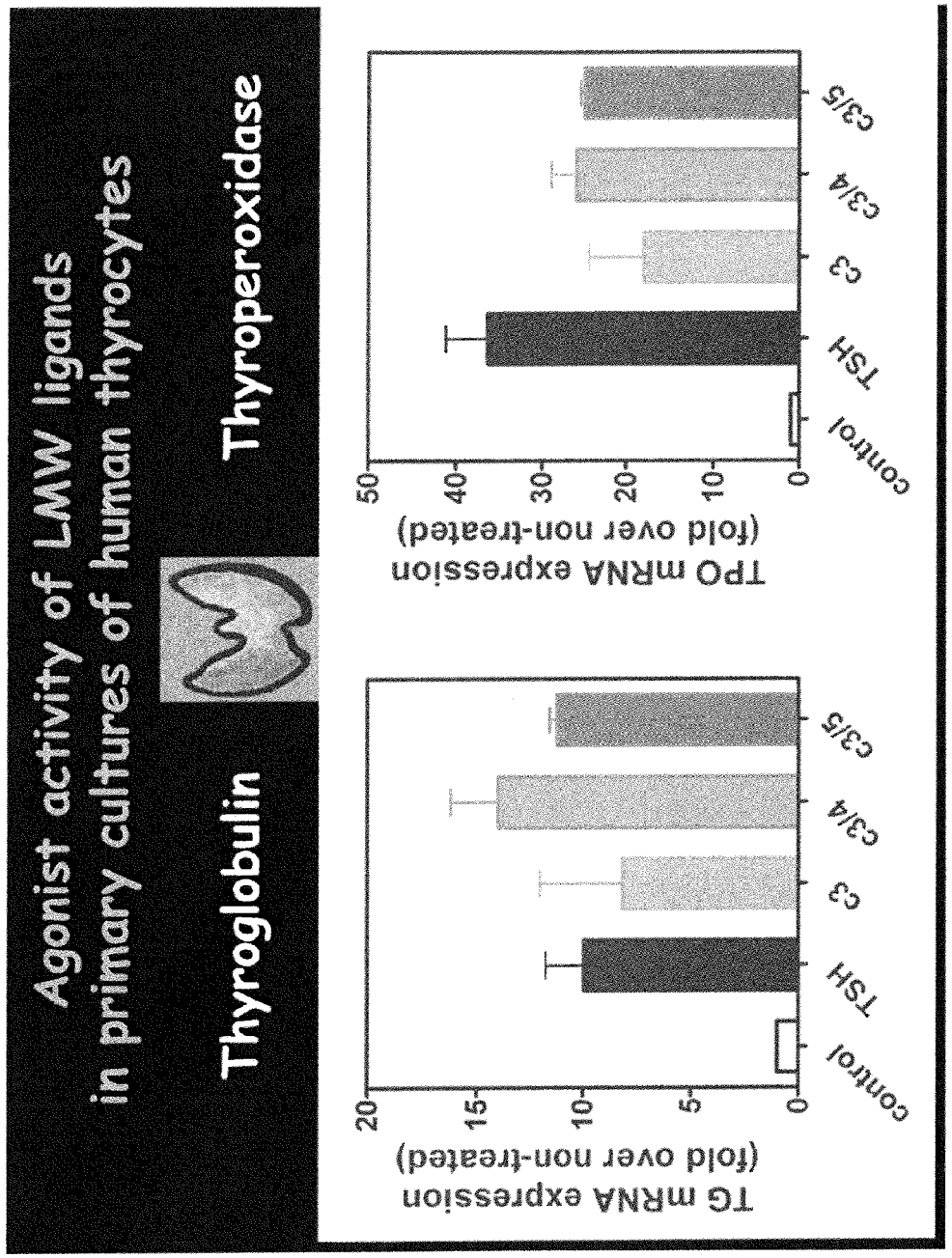
FIG. 3 is a graph of data for the agonist activity of several compounds disclosed herein in primary cultures of human thyrocytes.

FIG. 3 is a graph of data for the agonist activity of several compounds disclosed herein in primary cultures of human thyrocytes.

Because we identified the compounds disclosed herein using HEK EM 293 cells stably expressing TSHR, we sought to confirm their activities in primary cultures of human thyrocytes. Since TSH up-regulates expression of thyroid specific genes, we tested compounds disclosed herein on expression of mRNAs for thyroglobulin (TG) and thyroperoxidase (TP0). After 24 h, treatment of thyrocytes with 30 uM compounds disclosed herein increased TG mRNA expression to a level similar to TSH whereas TSHR small agonists increased TP0 mRNA expression but to lower levels than bTSH. This demonstrates that these ligands are active in primary cultures of human thyrocytes that express TSHR at physiological levels.

Culture of Primary Human Thyrocytes

Thyroid tissue samples were obtained through the National Institutes of Health Clinical Center during surgery for unrelated reasons. Patients provided informed consent on an IRB approved protocol and materials were received anonymously via approval of research activity through the Office of Human Subjects Research. The specimens were maintained in HBSS on ice and isolation of cells was initiated within 4 h after surgery. All preparations were performed under sterile conditions. Tissue samples were minced into small pieces by fine surgical forceps and scissors in a 10 cm dish with a small volume of HBSS. Tissue pieces were transferred to a 15 ml tube (Falcon) and washed at least 3 times with HBSS. Afterwards, tissue pieces were incubated with HBSS containing 3 mg/ml Collagenase Type IV (Gibco). Enzymatic digestion proceeded for 30 min or longer with constant shaking in a water bath at 37° C. until a suspension of isolated cells was obtained. After centrifugation for 5 min at 1000 rpm, the supernatant was removed and cells were resuspended in 10 ml DMEM with 10% FBS. Cells were plated in 10 cm tissue culture dishes and incubated at 37° C. in a humidified 5% $CO_2$ incubator. After 24 h, the supernatant containing non-adherent cells was removed. The primary cultures of thyroid cells formed a confluent monolayer within 5-7 days. For determination of thyroglobulin and thyroperoxidase mRNA expression, thyrocytes were seeded into 24-well plates at a density of $6 \times 10^4$ cells/well 24 h before the experiment.

Quantitative RT-PCR

Total RNA was purified using RNeasy Micro kits (Qiagen). First strand cDNA was prepared using a High Capacity cDNA Archive Kit (Applied Biosystems). RT-PCR was performed in 25 µl reactions using cDNA prepared from 100 ng of total RNA and Universal PCR Master Mix (Applied Biosystems). Primers and probes for thyroglobulin and thyroperoxidase were Assay-on-Demand (Applied Biosystems). Quantitative RT-PCR results were normalized to GAPDH to correct for differences in RNA input.

FIG. 4 is a graph of data of in vivo activity of a compound disclosed herein in mice We have shown in vitro using transfected cells that compounds disclosed herein activate the mouse TSHR with similar potency and efficacy as human TSHR. Because the known physiology of TSHRs is similar in mice and humans, in vivo studies in mice offer an ideal preclinical model for assessing possible clinical applications for these compound disclosed herein. We determined if one compound disclosed herein can activate TSHR when administered by intraperitoneal injection. 20 ug of the compound disclosed herein and 30 ug TSH in PBS containing 2% DMSO were administered to unanesthetized C57 BL/6 mice. The experimental endpoint was total thyroxine (T4) measurement in serum obtained from terminal retroorbital bleeds from anesthetized mice 2 hours after administration of the compound or TSH. Total T4 levels did rise after injection of TSH and of the compound disclosed herein.

In view of the many possible embodiments to which the principles of the disclosed compounds, compositions and methods may be applied, it should be recognized that the illustrated embodiments are only preferred examples and should not be taken as limiting the scope of the invention. Rather, the scope of the invention is defined by the following claims. We therefore claim as our invention all that comes within the scope and spirit of these claims.

What is claimed is:

1. A compound having formula I:

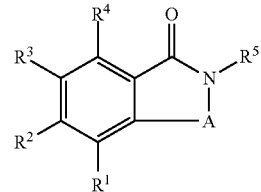

or a pharmaceutically acceptable salt thereof, wherein:

$R^1$-$R^4$ are each independently H, hydroxyl, alkyl, alkoxy, aminocarbonyl, or halogen;

$R^5$ is —$CH_2$-Ph, wherein Ph is a substituted phenyl;

A represents —N=C($R^{15}$)— (wherein a bond at the left end bonds to the benzene ring of formula I above and a bond at the right end bonds to the nitrogen heteroatom of formula I above) or —NH—CH($R^{15}$)— (wherein a bond at the left end bonds to the benzene ring of formula I above and a bond at the right end bonds to the nitrogen heteroatom of formula I above);

$R^{15}$ is represented by formula II:

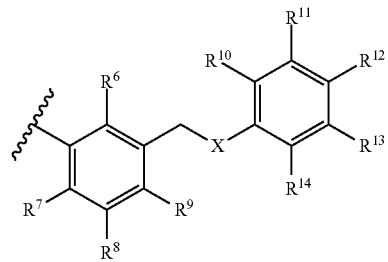

wherein:

$R^6$-$R^9$ are each independently H, hydroxyl, alkyl, or alkoxy;

$R^{10}$, $R^{11}$, $R^{13}$ and $R^{14}$ are each independently H;

$R^{12}$ is acetamido; and

X is O, S or N(H).

2. The compound of claim 1, wherein $R^9$ is $C_1$-$C_4$ is alkoxy.

3. The compound of claim 1, wherein X is O.

4. The compound of claim 1, wherein $R^1$-$R^4$ are each independently H.

5. The compound of claim 1, wherein $R^{15}$ is represented by formula III:

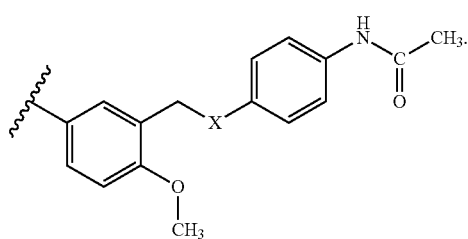

6. The compound oaf claim 1, wherein the compound is a thyroid stimulating hormone receptor agonist.

7. The compound of claim 1, wherein the compound is a selective thyroid stimulating hormone receptor agonist.

8. The compound of claim 1, wherein
$R^9$ methoxy; and
X is O or S.

9. A method for detecting thyroid cancer in a subject, comprising administering to the subject in need thereof a diagnostically effective amount of a compound of claim 1 and a diagnostically effective amount of radioiodine.

10. The method of claim 9, wherein the subject has undergone thyroidectomy for well-differentiated thyroid cancer.

11. The method of claim 9, wherein administration of the at least one compound of formula I enhances iodine uptake by thyroid cells.

12. A method for treating thyroid cancer in a subject, comprising administering to the subject in need thereof a therapeutically effective amount of a compound of claim 1.

13. The method of claim 12, further comprising co-administering radioiodine with the compound of formula I to ablate thyroid remnants following near-total thyroidectomy in a subject without evidence of metastatic disease.

14. The compound of claim 1, wherein $R^5$ is —$CH_2$-Ph wherein Ph is a phenyl substituted with chloro, phenyl, methoxy, trifluoromethyl, or methyl.

15. The compound of claim 5, wherein $R^5$ is —$CH_2$-Ph, wherein Ph is a phenyl substituted with chloro, phenyl, methoxy, trifluoromethyl, or methyl.

16. The compound of claim 1, wherein $R^5$ is —$CH_2$-Ph, wherein Ph is a phenyl substituted with 3-chloro.

17. The compound of claim 1, wherein
$R^9$ is methoxy;
X is O;
A is —NH—CH($R^{15}$)—; and
$R^1$-$R^4$ and $R^7$-$R^8$ are each independently H.

18. The compound of claim 17, wherein $R^5$ is —$CH_2$-Ph, wherein Ph is a phenyl substituted with 3-chloro.

19. The method of claim 9, wherein the radioiodine is radioiodine I-131.

20. The method of claim 9, wherein the method further comprises measuring serum thyroglobulin.

21. The method of claim 13, wherein the radioiodine is radioiodine I-131.

* * * * *